United States Patent
Hanton et al.

(10) Patent No.: US 9,447,202 B2
(45) Date of Patent: Sep. 20, 2016

(54) OLIGOMERISATION OF OLEFINIC COMPOUNDS WITH REDUCED POLYMER FORMATION

(71) Applicant: Sasol Technology (Proprietary) Limited, Rosebank (ZA)

(72) Inventors: Martin John Hanton, Fife (GB); David Matthew Smith, Fife (GB); William Fullard Gabrielli, Fife (GB); Stephen John Evans, Roodepoort (ZA)

(73) Assignee: SASOL TECHNOLOGY (PROPRIETARY) LIMITED, Rosebank (ZA)

( * ) Notice: Subject to any disclaimer, the term of this patent is extended or adjusted under 35 U.S.C. 154(b) by 0 days.

(21) Appl. No.: 14/399,103

(22) PCT Filed: May 8, 2013

(86) PCT No.: PCT/IB2013/053693
§ 371 (c)(1),
(2) Date: Nov. 5, 2014

(87) PCT Pub. No.: WO2013/168103
PCT Pub. Date: Nov. 14, 2013

(65) Prior Publication Data
US 2015/0152200 A1    Jun. 4, 2015

Related U.S. Application Data

(60) Provisional application No. 61/644,733, filed on May 9, 2012.

(51) Int. Cl.
| | | |
|---|---|---|
| *C08F 4/78* | (2006.01) | |
| *C08F 4/30* | (2006.01) | |
| *C08F 4/52* | (2006.01) | |
| *C07C 2/36* | (2006.01) | |
| *C08F 10/00* | (2006.01) | |

(52) U.S. Cl.
CPC . *C08F 4/78* (2013.01); *C07C 2/36* (2013.01); *C08F 4/30* (2013.01); *C08F 4/52* (2013.01); *C08F 10/00* (2013.01); *C07C 2531/14* (2013.01); *C07C 2531/24* (2013.01); *C07C 2531/34* (2013.01)

(58) Field of Classification Search
CPC .............. C08F 4/78; C08F 4/52; C08F 4/30; C08F 10/00; C07C 2/36; C07C 2531/14; C07C 2531/24; C07C 2531/34
See application file for complete search history.

(56) References Cited

U.S. PATENT DOCUMENTS

| | | | |
|---|---|---|---|
| 4,540,755 A | 9/1985 | Mayhew et al. | |
| 7,361,623 B2 * | 4/2008 | Dixon ................. | B01J 31/1805 502/103 |

FOREIGN PATENT DOCUMENTS

| | | | | |
|---|---|---|---|---|
| GB | WO 2011048527 A1 * | 4/2011 | ............... | C07C 2/32 |
| WO | WO 99/09075 | 2/1999 | | |
| WO | WO 03/053891 A1 | 7/2003 | | |
| WO | WO 2006/107373 A1 | 10/2006 | | |
| WO | WO 2009/108174 A1 | 9/2009 | | |
| WO | WO 2011/048527 A1 | 4/2011 | | |
| ZA | WO 2010092554 A1 * | 8/2010 | ............ | B01J 31/143 |

OTHER PUBLICATIONS

International Search Report from the European Patent Office for International Application No. PCT/IB2013/053593 mailed Sep. 6, 2013.
Written Opinion from the European Patent Office for International Application No. PCT/IB2013/053693 mailed May 9, 2014.

* cited by examiner

*Primary Examiner* — Ling Choi
*Assistant Examiner* — Catherine S Branch
(74) *Attorney, Agent, or Firm* — Finnegan Henderson Farabow Garrett & Dunner LLP

(57) ABSTRACT

A process for oligomerization of an olefinic compound for producing an oligomeric product is carried out in the presence of an activated catalyst, a non-metal oxygen containing additive and optionally a zinc compound. The oligomerization catalyst is an activated catalyst, which is provided by combining a source of chromium, a ligating compound, and a catalyst activator or combination of catalyst activators. The non-metal oxygen containing additive is present in an amount such that the ratio of the molar amount of the non-metal oxygen containing additive to the molar amount of chromium in the source of chromium per $10^6$ g/g Cr productivity is between 0.01 and 400.

25 Claims, No Drawings

OLIGOMERISATION OF OLEFINIC COMPOUNDS WITH REDUCED POLYMER FORMATION

TECHNICAL FIELD

This invention relates to the oligomerisation of olefinic compounds in the presence of an activated oligomerisation catalyst and relates further to the use of a non-metal oxygen containing additive in oligomerisation.

BACKGROUND OF THE INVENTION

A number of different oligomerisation technologies are known to produce α-olefins. Some of these processes, including the Shell Higher Olefins Process and Ziegler-type technologies, have been summarized in WO 04/056479 A1. The same document also discloses that the prior art (e.g. WO 03/053891 and WO 02/04119) teaches that chromium based catalysts containing heteroaromatic ligands with both phosphorus and nitrogen heteroatoms, selectively catalyse the trimerisation of ethylene to 1-hexene.

Processes wherein transition metals and heteroaromatic ligands are combined to form catalysts for trimerisation, tetramerisation, oligomerisation and polymerisation of olefinic compounds have also been described in different patent applications such as WO 03/053890 A1; WO 03/053891; WO 04/056479 A1; WO 04/056477 A1; WO 04/056480 A1; WO 04/056478 A1; WO 05/123884 A2; WO 05/123633 A1 and U.S. Pat. No. 7,285,607.

The catalysts utilized in the abovementioned trimerisation, tetramerisation, oligomerisation or polymerisation processes all include one or more activators to activate the catalyst. Suitable activators include organoaluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

A common catalyst activator used in combination with Cr based catalysts for oligomerisation of olefinic compounds is alkylaluminoxane, particularly methylaluminoxane (MAO). It is well known that MAO includes significant quantities of alkylaluminium in the form of trimethylaluminium (TMA), and in effect the catalyst activator is a combination of TMA and MAO. The MAO may also be replaced with modified MAO (MMAO), which may contain free trialkylaluminium in the form of TMA and heavier trialkylaluminiums. The use of organoboron compounds as catalyst activators is also known.

Activators containing aluminium compounds are costly to the effect that it impacts significantly on process economics of olefin oligomerisation technologies that utilize this class of activators. For this reason, it is desirable to run commercial oligomerisation processes at low activator concentrations. However, in the case where an aluminium-containing compound was used as an activator for transition metal based oligomerisation catalysts, it was found that at conditions of low starting aluminium concentrations (e.g. <6 mmol/l), low reaction rates and high levels of unwanted solid formation (polyethylene (PE) and waxes) resulted when ethylene was oligomerised.

Reduction in the formation of polymers as a by-product in Cr-based ethylene oligomerisation (both tri- and tetramerisation) processes remains an ongoing challenge, as polymer fouling reduces plant run time and necessitates shut-downs due to blockages. Furthermore, high catalyst activity must accompany low polymer formation in order that good space-time yields are obtained, and high catalyst productivity is required in order to maintain acceptable economic performance.

Generally speaking, the literature teaches towards the removal of impurities, specifically oxygen, from the system before ethylene polymerisation or oligomerisation catalysis is performed (see US2010/0081777A1 and US2011/0282016A1 for example) as oxygen is considered a poison (see M. P Daniels and S. J. Martin, J. Phys. Chem. 1991, 95, 3289-3293).

SUMMARY OF THE INVENTION

According to an aspect of the present invention, there is provided a process for producing an oligomeric product by the oligomerisation of at least one olefinic compound, the process including:
a) providing an activated oligomerisation catalyst by combining, in any order,
   i) a source of chromium;
   ii) a ligating compound of the formula

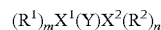

wherein $X^1$ and $X^2$ are independently an atom selected from the group consisting of nitrogen, phosphorus, and oxygen, or an oxidised nitrogen or phosphorus atom where the valence of $X^1$ and/or $X^2$ allows for such oxidation;
   Y is a linking group between $X^1$ and $X^2$;
   m and n are independently 1 or 2; and
   $R^1$ and $R^2$ are independently hydrogen, a hydrocarbyl group, an organoheteryl group, a heterohydrocarbyl group, a substituted hydrocarbyl group or a substituted heterohydrocarbyl group, and each $R^1$ being the same or different when m>1, and each $R^2$ being the same or different when n>1; and
   iii) a catalyst activator or combination of catalyst activators; and
b) contacting at least one olefinic compound with the activated oligomerisation catalyst in the presence of a non-metal oxygen containing additive, which non-metal oxygen containing additive may be introduced together with the activated catalyst, after introduction of the activated catalyst but prior to introduction of the olefinic compound, together with the olefinic compound, or after the olefinic compound has contacted the activated catalyst, the non-metal oxygen containing additive being present in an amount such that the ratio of the molar amount of the non-metal oxygen containing additive to the molar amount of chromium in the source of chromium per $10^6$ g/g Cr productivity is between 0.01 and 400.

According to a further aspect of the present invention there is provided a process for activating an oligomerisation catalyst suitable for use in producing an oligomeric product from at least one olefinic compound, the process comprising combining, in any order,
i) a source of chromium;
ii) a ligating compound of the formula

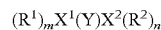

wherein $X^1$ and $X^2$ are independently an atom selected from the group consisting of nitrogen, phosphorus, and oxygen, or an oxidised nitrogen or phosphorus atom where the valence of $X^1$ and/or $X^2$ allows for such oxidation;

Y is a linking group between $X^1$ and $X^2$;

m and n are independently 1 or 2; and $R^1$ and $R^2$ are independently hydrogen, a hydrocarbyl group, an organoheteryl group, a heterohydrocarbyl group, a substituted hydrocarbyl group or a substituted heterohydrocarbyl group, and $R^1$ being the same or different when m>1, and $R^2$ being the same or different when n>1;

iii) a catalyst activator or combination of catalyst activators; and iv) a non-metal oxygen containing additive, the non-metal oxygen containing additive being present in an amount such that the ratio of the molar amount of the non-metal oxygen containing additive to the molar amount of chromium per $10^6$ g/g Cr productivity in the source of chromium is between 0.01 and 400.

In some embodiments of the invention the non-metal oxygen containing additive is present in an amount such that the ratio of the molar amount of the non-metal oxygen containing additive to the molar amount of chromium in the source of chromium per $10^6$ g/g Cr productivity is between 0.01 and 200, or 0.01 and 100, or between 0.1 and 50, or between 0.1 and 20, or between 0.2 and 10.

In some embodiments of the invention, the process may include the use of a solvent.

Some embodiments of the invention may utilise a zinc compound, which in some embodiments is a diethyl zinc compound.

DETAILED DESCRIPTION OF EMBODIMENTS OF THE INVENTION

The invention relates to a process for oligomerisation of an olefinic compound for producing an oligomeric product. The process is carried out in the presence of an activated catalyst, a non-metal oxygen containing additive and optionally a zinc compound. The oligomerisation catalyst is an activated catalyst, which is provided by combining a source of chromium, a ligating compound, and a catalyst activator or combination of catalyst activators.

In this specification, the following definitions apply:

The term "olefinic compound" denotes an olefin or any compound which includes a carbon to carbon double bond and "olefinic moiety" has a corresponding meaning;

A "hydrocarbyl group" as per IUPAC is a univalent group formed by removing one hydrogen atom from a hydrocarbon;

A "hydrocarbylene group" as per IUPAC is a divalent group formed by removing two hydrogen atoms from a hydrocarbon the free valencies of which are not engaged in a double bond;

A "heterohydrocarbyl group" is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

A "heterohydrocarbylene group" is a divalent group formed by removing two hydrogen atoms from either one or two carbon atoms of an organic molecule containing at least one heteroatom the free valencies of which are not engaged in a double bond;

An "organoheteryl group" as per IUPAC is a univalent group containing carbon, which are thus organic but which have their free valence at an atom other than carbon;

A "polar substituent" is a substituent with a permanent electric or induced dipole moment; and A "non-polar substituent" is a substituent without a permanent electric or induced dipole moment.

The oligomerisation catalyst of the present invention, in some embodiments, is a trimerisation catalyst or a tetramerisation catalyst or both, preferably a tetramerisation catalyst.

In some embodiments of the invention, the oligomerisation process for producing an oligomeric product is a trimerisation process for producing a trimeric product by the utilization of a trimerisation catalyst; in some embodiments it is a tetramerisation process for producing a tetrameric product by utilization of a tetramerisation catalyst; whilst in yet other embodiments of the invention it is both.

The inventors of the present invention have surprisingly found that the incorporation of a non-metal oxygen containing additive in the oligomerisation process described above, within the ranges described above, results in three benefits: i) an increase in catalyst activity (rate); ii) an increase in catalyst productivity (lifetime); and iii) a reduction in solids formation, that is, polymer and in particular polyethylene formation relative to processes in which such non-metal oxygen containing additive is absent. This is surprising as a person skilled in the art of ethylene oligomerisation is taught that a general prerequisite is to exclude poisons, primarily oxygen/air. Hence, it was surprising to find that when a very low level of oxygen was added to the reaction the beneficial effects listed above were observed. It was also found that the range over which such a positive effect is observed is quite narrow. Too little oxygen and no benefit is observed, too much oxygen and the poisoning effect of oxygen returns, with activity and productivity being ameliorated, whilst polymer formation increases again. Hence, there is a clear optimum range for addition of the non-metal oxygen containing additive, where a maxima in the positive effects exists.

Oligomerisation Catalyst

Source of Chromium (I):

The source of chromium may be an inorganic salt, an organic salt, a coordination compound or an organometallic complex.

In some embodiments of the invention the source of chromium is selected from the group consisting of chromium trichloride tris-tetrahydrofuran complex; (benzene) tricarbonyl chromium; chromium (III) octanoate; chromium hexacarbonyl; chromium (III) acetylacetonate, chromium (III) naphthenate, chromium (III) 2-ethylhexanoate, chromium (III) acetate, chromium (III) 2,2,6,6-tetramethylheptadionate, chromium (III) chloride. In some embodiments it is chromium (III) acetylacetonate or chromium (III) 2-ethylhexanoate.

Ligating Compound (ii):

The ligating compound of the invention is generally a compound of formula

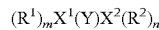

$(R^1)_m X^1(Y)X^2(R^2)_n$

In some embodiments, $X^1$ and $X^2$ are independently an atom selected from the group consisting of nitrogen, phosphorus, and oxygen, or an oxidised nitrogen or phosphorus atom where the valence of $X^1$ and/or $X^2$ allows for such oxidation.

In some embodiments, $X^1$ and/or $X^2$ are independently a phosphorus atom or an oxidised phosphorus atom. In some embodiments $X^1$ and $X^2$ are P and N, respectively, whilst in other embodiments $X^1$ and/or $X^2$ are the same, and are both P.

Y is a linking group, as defined more fully below.

It will be appreciated that m and n are dependent on factors such as the valence and oxidation state of $X^1$ and $X^2$, bond formation of Y with $X^1$ and $X^2$, respectively, and bond formation of $R^1$ and $R^2$ with $X^1$ and $X^2$, respectively. In some embodiments both m and n are independently 1 or 2.

In some embodiments the ligating compound is a bidentate ligand.

In some embodiments the ligating compound is of the formula

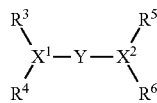

wherein Y is as defined more fully below, $X^1$ and $X^2$ are independently selected from the group consisting of nitrogen and phosphorus, and $R^3$ to $R^6$ are each independently a hydrocarbyl group or a heterohydrocarbyl group.

In some embodiments $X^1$ and $X^2$ are the same. In some embodiments $X^1$ and $X^2$ are phosphorus.

$R^3$ to $R^6$ may independently be selected from the group consisting of a non-aromatic moiety; an aromatic moiety; and a heteroaromatic moiety. In some embodiments each of $R^3$ to $R^6$ is an aromatic or heteroaromatic moiety, in particular an aromatic moiety (including a substituted aromatic moiety). The aromatic moiety (or substituted aromatic moiety) may comprise phenyl or a substituted phenyl.

In some embodiments, one or more of $R^3$ to $R^6$ may be a substituted hydrocarbyl group or a substituted heterohydrocarbyl group, of which at least one substituent is bound to a hydrocarbyl group or a heterohydrocarbyl group. In other embodiments, one or more of $R^3$ to $R^6$ may be a hydrocarbyl group or a heterohydrocarbyl group.

In this specification, a substituent with reference to moieties bound to $X^1$ and/or $X^2$ is a moiety (excluding H) that is bound to a linear structure or a cyclic structure bound to $X^1$ and/or $X^2$, but the substituent does not form part of the linear or cyclic structure.

The linear or cyclic structure may be selected from the group consisting of a linear hydrocarbyl, a linear heterohydrocarbyl, a cyclic hydrocarbyl and a cyclic heterohydrocarbyl group. Linear hydrocarbyl may include methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl.

Linear heterohydrocarbyl may include methoxy, ethoxy, thiomethoxy, thioethoxy, methylsilyl, ethylsilyl, methylamino, methylphosphino, methoxymethyl and thiomethoxymethyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl.

$R^3$ to $R^6$ may also be selected from a group of metallocenes such as a ferroceneyl, zirconoceneyl and titanoceneyl group.

In some embodiments $R^3$ to $R^6$ are aromatic moieties of which a ring atom of the aromatic ring structure is bound to either $X^1$ or $X^2$ and with a polar substituent bound to a ring atom of the aromatic ring structure adjacent to the ring atom bound to $X^1$ or $X^2$. Any of $R^3$ to $R^6$ may independently be ortho-substituted with a halogen selected from the group consisting of fluorine, chlorine or bromine, such that none, one, two, three or four of $R^3$ to $R^6$ are ortho-substituted with a halogen. In some embodiments the halogen is fluorine. Alternatively, each of $R^3$ to $R^6$ may independently be ortho-substituted with either a halogen selected from the group consisting of fluorine, chlorine or bromine or ortho-substituted with an alkyl group. In some embodiments the halogen is fluorine and the alkyl is methyl or ethyl. $R^3$ to $R^6$ may be selected such that any combination of no substitution, ortho-substitution with halogen and ortho-substitution with alkyl are present.

If two or more of $R^3$ to $R^6$ are aromatic moieties with a ring atom of the aromatic ring structure bound to either $X^1$ or $X^2$, in some embodiments not more than two of said aromatic moieties $R^3$ to $R^6$ have a substituent bound to a ring atom of the aromatic ring structure adjacent to the ring atom bound to $X^1$ or $X^2$.

In one embodiment of the invention, $R^3$ to $R^6$ are the same or different and each is a hydrocarbyl group, or a heterohydrocarbyl group which contains no substituent or contains a non-polar substituent. In some embodiments each of $R^3$ to $R^6$ does not include any polar substituent. In one embodiment of the invention at least two of (but in particular all of $R^3$ to $R^6$ are aromatic moieties with a ring atom of the aromatic ring structure bound to $X^1$ or $X^2$, and in some embodiments not more than two of said aromatic moieties $R^3$ to $R^6$ have a non-polar substituent other than H bound to a ring atom of the aromatic ring structure adjacent to the ring atom bound to $X^1$ or $X^2$.

In some embodiments none of the aromatic moieties $R^3$ to $R^6$ have a non-polar substituent bound to a ring atom of the aromatic ring structure adjacent to the ring atom bound to $X^1$ or $X^2$. In some embodiments all of aromatic moieties $R^3$ to $R^6$ are non-substituted aromatic moieties.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may independently be linked to one or more of each other, or to Y to form a cyclic structure.

$R^3$ and $R^4$ may be the same and $R^5$ and $R^6$ may be the same. $R^3$ to $R^6$ may all be the same.

In other embodiments of the invention, $R^3$ to $R^6$ are the same or different and each is a hydrocarbyl group, or a heterohydrocarbyl group (in particular an organyl group), provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may independently be selected from the group consisting of a substituted non-aromatic moiety; a substituted aromatic moiety; and a substituted heteroaromatic moiety. In some embodiments each of $R^3$ to $R^6$ is a substituted aromatic or a substituted heteroaromatic moiety, in particular a substituted aromatic moiety. The substituted aromatic moiety may comprise a substituted phenyl. In one embodiment of the invention at least two of (in particular all of) $R^3$ to $R^6$ are aromatic with a ring atom of the aromatic ring structure bound to $X^1$ or $X^2$, but particularly not more than two of said aromatic moieties $R^3$ to $R^6$ have a substituent bound to a ring atom of the aromatic ring structure adjacent to the ring atom bound to $X^1$ or $X^2$.

Any polar substituent on one or more of $R^3$, $R^4$, $R^5$ and $R^6$ may be electron donating.

Suitable polar substituents may be a methoxy, ethoxy, isopropoxy, $C_3$-$C_{20}$alkoxy, phenoxy, methoxymethyl, methylthiomethyl, 1,3-oxazolyl, methoxymethoxy, hydroxyl, amino, tosyl, methylsulfanyl, trimethylsiloxy, dimethylamino, sulphate, nitro, halides or the like.

In some embodiments of the invention, Y may be selected from the group consisting of an organic linking group such as a hydrocarbylene, substituted hydrocarbylene, heterohydrocarbylene and a substituted heterohydrocarbylene; an inorganic linking group comprising either a single- or two-atom linker spacer; and a group comprising methylene; dimethylmethylene; ethylene; ethene-1,2-diyl; propane-1,2-diyl, propane-1,3-diyl; cyclopropane-1,1-diyl; cyclopropane-1,2-diyl; cyclobutane-1,2-diyl, cyclopentane-1,2-diyl, cyclohexane-1,2-diyl, cyclohexane-1,1-diyl; 1,2-phenylene; naphthalene-1,8-diyl; phenanthrene-9,10-diyl, phenanthrene-4,5-diyl, 1,2-catecholate, 1,2-diarylhydrazine-1,2-diyl (—N(Ar)—N(Ar)—) where Ar is an aryl group; 1,2-dialkylhydrazine-1,2-diyl (—N(Alk)-N(Alk)-) where Alk is an alkyl group; —B($R^7$)—, —Si($R^7$)$_2$—, —P($R^7$)— and —N($R^7$)— where $R^7$ is a hydrocarbyl (—$C_nH_{2n+1}$) or cyclic hydrocarbyl (—$C_nH_{2n-1}$) or heterocarbyl or cyclic heterocarbyl or halogen. In some embodiments, Y may be —N($R^7$)— and $R^7$ may be selected from the group consisting of alkyl, substituted alkyl, aryl, substituted aryl, aryloxy, substituted aryloxy, halogen, alkoxycarbonyl, alkoxy, aminocarbonyl, dialkylamino, silyl group or derivative thereof, and aryl substituted with any of these substituents. In some embodiments $R^7$ may be a hydrocarbyl or a heterohydrocarbyl or an organoheteryl group. $R^7$ may be methyl, ethyl, propyl, isopropyl, cyclopropyl, allyl, butyl, tertiary-butyl, sec-butyl, cyclobutyl, pentyl, isopentyl, 1,2-dimethylpropyl (3-methyl-2-butyl), 1,2,2-trimethylpropyl(R/S-3,3-dimethyl-2-butyl), 1-(1-methylcyclopropyl)-ethyl, neopentyl, cyclopentyl, cyclohexyl, cycloheptyl, cyclo-octyl, decyl, cyclodecyl, 1,5-dimetylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxysilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl.

In some embodiments of the invention the ligating compound is of the formula

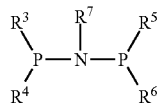

with $R^3$ to $R^7$ as defined above.

In some embodiments, each of $R^3$ to $R^6$ is an alkyl (in particular methyl, ethyl or isopropyl) or aromatic (in particular phenyl or substituted phenyl).

The ligating compound may include a polymeric moiety to render the reaction product of the source of chromium and the said ligating compound to be soluble at higher temperatures and insoluble at lower temperatures e.g. 25° C. This approach may enable the recovery of the complex from the reaction mixture for re-use and has been used for another catalyst as described by D. E. Bergbreiter et al., *J. Am. Chem. Soc.*, 1987, 109, 177-179. In a similar vein these chromium catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P (phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N (methyl)P(p-methoxyphenyl)$_2$)-benzene.

The ligating compounds may be prepared using procedures known to one skilled in the art and procedures forming part of the state of the art.

The oligomerisation catalyst may be prepared in situ, that is in the reaction mixture in which the oligomerisation reaction is to take place. Often the oligomerisation catalyst will be prepared in situ. Alternatively the catalyst may be pre-formed or partly pre-formed.

Activation
Activator (iii)

The catalyst activator may be a compound that generates an active catalyst when the activator is combined with the source of chromium and the ligating compound.

These activators may be the same or similar to those found to be useful for activating transition-metal-based olefin polymerisation catalysts, a review of which is provided by Marks [*Chem Rev.* 2000, 100, 1391-1394]. Mixtures of activators may also be used.

Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula AlR$_3$, where each R is independently $C_1$-$C_{12}$ alkyl, oxygen or halide, and compounds such as LiAlH$_4$ and the like. Examples include trimethylaluminum (TMA), triethylaluminum (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula [R⁸AlO]$_s$ and the linear aluminoxanes by the formula R⁹(R¹⁰AlO)$_s$ wherein s is a number from about 2 to 50, and wherein R⁸, R⁹, and R¹⁹ represent hydrocarbyl groups, particularly $C_1$ to $C_6$ alkyl groups, for example methyl, ethyl or butyl groups. Alkylaluminoxanes especially methylaluminoxane (MAO) are preferred in some embodiments. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminium (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerisation and are disclosed in more detail in for example, U.S. Pat. Nos. 5,491,272; 5,750,817; 5,856,257; 5,910,619; and 5,919,996 as well as WO2008/146215 and WO2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that the preferred quantity employed is 0.5 to 2000 moles of aluminium per mole of chromium.

Examples of suitable organoboron activator compounds are boroxines, NaBH$_4$, trimethylboron, triethylboron, triphenylboron, dimethylphenylammoniumtetra(phenyl)borate, trityltetra(phenyl)borate, dimethylphenylammoniumtetrakis(pentafluorophenyl)borate, trityltetrakis(pentafluorophenyl)borate, tris(pentafluorophenyl) boron, sodium tetrakis[(bis-3,5-trifluoromethyl)phenyl]borate, dimethylphenylammoniumtetrakis[(bis-3,5-trifluoromethyl)phenyl]borate, and trityltetrakis[bis-3,5-trifluoromethyl)phenyl]borate.

Those skilled in the art will recognise that boron-containing activators are commonly used in combination with aluminium alkyl activators.

In some embodiments of the invention organoboron activators, as described in WO2010/092554, include a cation and a non-coordinating anion of the general formula

[(R)$_x$L*-H]⁺[B(R¹¹)$_4$]⁻ wherein:
L* is an atom selected from the group consisting of N, S and P;
the cation [(R)$_x$L*-H]⁺ is a Bronsted acid;
x is an integer 1, 2 or 3;
each R is the same or different and each is a —H, hydrocarbyl group or a heterohydrocarbyl group;
provided that at least one R comprises at least 6 carbon atoms and provided further that the total number of carbon atoms in (R)$_x$ collectively is greater than 12;
R¹¹ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl) borate and trioctylammoniumtetrakis(pentafluorophenyl) borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

Other preferred activators, as described in WO2007/039851, include a cation and an anion component, and may be represented by the following formula:

$$(L-H)^{d+}(A^{d-})$$

where L is a neutral Lewis base; H is hydrogen; (L-H)$^{d+}$ is a Bronsted acid; A$^{d-}$ is a non-coordinating anion having the charge d; and d is an integer from 1 to 3.

In these activator compounds, A$^{d-}$ can be a fluorinated aluminate group. Illustrative but non-limiting examples of the anion component A$^{d-}$ are [Al{OC(CF$_3$)$_3$}$_4$]⁻; [Al(OC$_6$F$_5$)$_4$]⁻; [Al(C$_6$F$_4$O$_2$)$_2$]⁻; [AlF{OC(CF$_3$)$_3$}$_3$]⁻; [Al$_2$F{OC(CF$_3$)$_3$}$_6$]⁻; and [Ta(OC$_6$F$_5$)$_6$]⁻.

The activator compound may optionally be a solid material, or be supported on an insoluble solid material. For example, aluminoxanes such as MAO and borate activators may be supported on inorganic oxides such as alumina, silica, MgCl$_2$ or the like.

Co-Activator

In some embodiments of the invention the co-activator is an organoaluminium compound and/or an organoboron compound. Alternatively it may be an organic salt such as methyl lithium and/or methyl magnesium bromide, or an inorganic acid or salt such as tetrafluoroboric acid etherate, silver tetrafluoroborate, sodium hexafluoroantimonate, and the like.

Examples of suitable organoboron compounds are boroxines, triethylborane, tris(pentafluorophenyl)borane, tributylborane and the like.

Suitable organoaluminium compounds include compounds of the formula Al(R¹²)$_3$ (R¹² being the same or different), where each R¹² is independently an organyl group, a halogenated organyl group or a halide, with at least one of R⁹ being an organyl group or a halogenated organyl group. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes.

Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

In an embodiment of the invention the co-activator may comprise a compound of the formula M'(R')$_n$.

wherein

M' is selected from the group consisting of a group 3A atom, a group 4A atom and a metal atom, including an alkali metal atom and an alkaline earth metal atom;

n is 1 or a larger integer; and

R' is an organic group, R' being the same or different when n is larger than 1.

In some embodiments M' is selected from the group consisting of a group 3A atom, a group 4A atom, and a transition metal atom. In some embodiments the R group is bound to a group 3A atom. In some embodiments the group 3A atom is selected from the group consisting of Al and B, in particular it is Al.

The organic group R may be an organyl group, and in some embodiments it comprises a hydrocarbyl group, in some embodiments it comprises an alkyl group, and in some embodiments methyl, ethyl or a larger alkyl group.

In one embodiment of the invention the co-activator comprises $AlR''_3$ wherein R'' is an alkyl group.

The co-catalyst may be selected from the group consisting of trimethylaluminium (TMA); triethylaluminium (TEA), tributylaluminium, tri-isobutylaluminium (TIBA) and tri-n-octylaluminium.

It will be appreciated that TMA is relatively expensive and accordingly the use thereof may be wished to be avoided. It has been found that by using an activator as defined in the present invention in combination with a co-activator as defined above (but excluding MAO) the use of TMA can be avoided as a co-catalyst.

It is foreseen that a co-activator as defined hereinabove will usually be used in combination with an activator as defined above.

In use, where both an activator and a co-activator are used, the co-activator may be added first and the activator may be added subsequently.

Zinc Compound

An additive can be used in the form of a zinc-containing species. The species can be any form of zinc or any zinc containing compound. The zinc compound may undergo reaction in situ with the trialkylaluminium to form a new zinc species in situ.

Specific examples of suitable zinc compounds include zinc, activated zinc, zinc halides, zinc alkyls, zinc oxygenates (including zinc acetate, acetylacetonates and carboxylates) and zinc porphyrin. In some embodiments, the zinc compound is zinc dialkyl, in particular dimethyl zinc or diethyl zinc.

The zinc compound is present in the reaction of the invention in an amount such that the ratio of the molar amount of zinc in the zinc compound to the molar amount of chromium in the source of chromium is between 1 and 10000, or between 10 and 1000, or between 50 and 450.

The zinc may be used as any concentration of stock solution and the concentration in situ in the reactor should be between 0.0001 mmol/L and 1 mol/L, or between 0.001 mmol/L and 0.1 mol/L, or between 0.01 mmol/L and 0.01 mol/L.

The zinc compound may be added at any stage during the activation process, in some embodiments it is added directly to the reactor. The zinc may be used as a mixed stock solution with the trialkylaluminium, or with any other component.

Non-Metal Oxygen Containing Additive

The non-metal oxygen containing additive can be gaseous, liquid or solid. It can be used in pure form, or added entrained in a gas or as a stock solution or absorbed or adsorbed onto a solid, where it can be mixed with other components of the catalyst system.

In some embodiments of the invention, the non-metal oxygen containing additive can be selected from the group consisting of dioxygen ($O_2$), ozone ($O_3$), nitrous oxide ($N_2O$), sulphur dioxide ($SO_2$), epoxide (such as ethylene oxide, propylene oxide, butylene oxide, or the epoxide of any olefin), peroxides (such as $H_2O_2$ or organic peroxides ROOH, where R is hydrocarbyl or heterohydrocarbyl), amine oxides (such as pyridinium N-oxide, TEMPO, $R_3NO$) or mixtures thereof.

In some embodiments the non-metal oxygen containing additive can be selected from the group consisting of dioxygen ($O_2$), ozone ($O_3$), nitrous oxide ($N_2O$) and sulphur dioxide ($SO_2$), epoxide (such as ethylene oxide and propylene oxide) or mixtures thereof. In some embodiments the non-metal oxygen containing additive is nitrous oxide or dioxygen or mixtures thereof. In some embodiments the non-metal oxygen containing additive is dioxygen.

When the non-metal oxygen containing additive is a gas, it can be added as a pure gas directly to the headspace of the reaction, directly into reaction solution or with another reagent. It can be added as a mixture with another inert gas, such as dinitrogen or argon or it can be added as a mixture with an olefinic gas such as ethylene or propylene. This gas mixture can be added directly to the headspace of the reaction, directly into reaction solution or with another reagent. If the non-metal oxygen containing additive is dioxygen it can be added as air, compressed or uncompressed or mixed with another inert gas, such as dinitrogen or argon, or mixed with an olefinic gas such as ethylene or propylene.

When the non-metal oxygen containing additive is gaseous and used as a mixture with another gas, such a mixture may be prepared by any practical means that gives the composition required, including but not limited to: use of pre-prepared gas mixtures; mixing of the additive gas and carrier gas via flow-metering, combination of flows via capillary techniques or similar; or passage of the carrier gas past a porous membrane with the additive gas on the other side.

When the non-metal oxygen containing additive is gaseous and used as a solution in a suitable liquid medium, for example the reaction solvent, such a solution of the additive gas or additive gas as a mixture in another gas may be prepared by any practical means that gives the composition required, including but not limited to: sparging the liquid medium with the additive gas or additive gas as a mixture in another gas; vacuum degassing the liquid medium and back-filling with the additive gas or additive gas as a mixture in another gas; or passage of the liquid medium past a porous membrane with the additive gas or additive gas as a mixture in another gas on the other side.

When the non-metal oxygen containing additive is gaseous or liquid and added absorbed or adsorbed onto a solid carrier (for example molecular sieves, alumina, silica), this may be prepared by any practical means, including but not limited to: pressurisation of the solid with the gaseous or liquid oxygen containing additive, with or without heating or cooling; or activation of the solid under vacuum with or without heating or cooling, sonication or irradiation, followed by exposure with or without elevated pressure to the gaseous or liquid additive.

When the non-metal oxygen containing additive is liquid or solid and has suitable vapour pressure such that it can be used as a mixture with a gas, such a mixture can be prepared by any practical means, including but not limited to: use of a pre-prepared mixture; passage of the gas over or through the additive, which may or may not be heated, agitated, sonicated or irradiated; passage of the gas past a porous membrane with the liquid or solid non-metal oxygen containing additive on the other side.

When the non-metal oxygen containing additive is liquid or solid and is used as a solution in another liquid medium, for example the reaction solvent, such a mixture may be prepared by any practical means commonly employed for dissolution.

When the non-metal oxygen containing additive is liquid or solid and used in pure form it can be added to the reaction to the headspace or liquid phase via any practical means.

A mixture of oxygen containing additives may be used, where the non-metal oxygen containing additives may be combined in any ratio, and added simultaneously or subsequently, and may be added via the same or different means.

The non-metal oxygen containing additive is present in the reaction of the invention in an amount such that the ratio of the molar amount of the non-metal oxygen containing additive to the molar amount of chromium in the source of chromium per $10^6$ g/g Cr productivity is between 0.01 and 400, or between 0.01 and 200, or between 0.1 and 20, or between 0.2 and 10.

It has surprisingly been found that the range over which the additive works is quite narrow, and that both above and below this range a detrimental effect exists. Too little non-metal oxygen containing additive and no benefit is observed, too much non-metal oxygen containing additive and the poisoning effect of non-metal oxygen containing additive returns, with activity and productivity being ameliorated, whilst polymer formation increases again. Hence, there is a clear optimum range for addition of the non-metal oxygen containing additive, where a maxima in the positive effects exists.

Olefinic Compound to be Oligomerised

The olefinic compound may comprise a single olefinic compound or a mixture of olefinic compounds. In one embodiment of the invention it may comprise a single olefin.

The olefin may include multiple carbon-carbon double bonds, but in some embodiments it comprises a single carbon-carbon double bond. The olefin may comprise an α-olefin with 2 to 30 carbon atoms, or 2 to 10 carbon atoms. The olefinic compound may be selected from the group consisting of ethylene, propene, 1-butene, 1-pentene, 1-hexene, 1-heptene, 1-octene, 1-nonene, 1-decene, 3-methyl-1-pentene, 3-methyl-1-pentene, 4-methyl-1-pentene, styrene, p-methyl styrene, 1-dodecene or combinations thereof. In some embodiments it comprises ethylene or propene, in particular ethylene. The ethylene may be used to produce hexene and/or octene, in particular 1-hexene and/or 1-octene.

Oligomerisation

The oligomerisation process may comprise a trimerisation process, alternatively or additionally it may comprise a tetramerisation process.

The process may be oligomerisation of two or more different olefinic compounds to produce an oligomer containing the reaction product of the two or more different olefinic compounds. In some embodiments, however, the oligomerisation (particularly trimerisation and/or tetramerisation) comprises the oligomerisation of a single monomer olefinic compound.

In one embodiment of the invention the oligomerisation process is oligomerisation of a single α-olefin to produce an oligomeric α-olefin. Typically it comprises the trimerisation and/or tetramerisation of ethylene, in paricularto1-hexene and/or 1-octene.

Oligomeric Product

The oligomeric product may be an olefin, or a compound including an olefinic moiety. In some embodiments the oligomeric product includes an olefin, in some embodiments an olefin containing a single carbon-carbon double bond, and in some embodiments it includes an α-olefin. The olefin product may include hexene, in particular 1-hexene, or it includes octene, in particular 1-octene. In an embodiment of the invention the olefinic product includes a mixture of hexene and octene, in particular a mixture of 1-hexene and 1-octene.

In one embodiment of the invention the oligomerisation process is a selective process to produce an oligomeric product containing more than 30% by mass of a single olefin product. The olefin product may be hexene, in particular 1-hexene, or alternatively it may be octene, in particular 1-octene.

In some embodiments the product contains at least 35% of the said olefin, in particular α-olefin, but it may be more than 40%, 50%, or even 60% by mass.

The olefinic product may be branched, but in particular it is non-branched.

Catalyst Preparation

It is foreseen that i) the source of chromium and ii) the ligating compound may first be reacted together and the resulting product may even be isolated, before combining it with the catalyst activator iii) and optional zinc compound. However, i), ii), iii) and the zinc compound may be combined in any suitable order in the presence or absence of a solvent, but in particular at least some, but more particularly all of i), ii) and iii) are first combined and subsequently contacted with the olefinic compound to which the zinc compound has already been added. The non-metal oxygen containing additive may be introduced at any time during the catalyst preparation, and in some embodiments is introduced after combining i), ii) and iii), and optionally the zinc compound.

The contacting of the olefinic compound with compounds i) to iii), the optional zinc compound, and the non-metal oxygen containing additive preferably takes place under conditions to allow oligomerisation of the olefinic compound. These conditions are well known to a person skilled in the art and include elevated temperatures and pressure. The oligomerisation may be carried out at temperatures from 10° C. to 250° C., or from 15° C. to 130° C., or from 40° C. to 120° C. Oligomerisation may be carried out at a temperature of at least 0° C., or at least 40° C., or at least 50° C. It may be carried out at a pressure of at least 100 kPa, or at least 1000 kPa, or at least 3000 kPa.

The preparation of the activated catalyst may be carried out in a liquid medium, in some embodiments an inert liquid medium. The liquid medium may be the same liquid medium wherein the oligomerisation with the diluted catalyst is carried out.

The activated oligomerisation catalyst before dilution may be prepared in the same container as the one in which the diluted activated oligomerisation catalyst is contacted with the olefinic compound to be oligomerised. In some embodiments the activated oligomerisation catalyst before dilution is prepared in a separate container to the one in which the oligomerisation catalyst is contacted with the olefinic compound to be oligomerised.

The source of chromium and ligating compound may be combined to provide any suitable molar ratio, in some embodiments a chromium to ligand compound molar ratio from about 0.01:100 to 10000:1, or from about 0.1:1 to 10:1.

The zinc can be used in any loading compared to the chromium, in some embodiments between 1 and 10000, or between 10 and 1000, or between 50 and 450. The zinc can be used as any concentration of stock solution and the concentration in situ in the reactor can be between 0.0001 mmol/L and 1 mol/L, or between 0.001 mmol/L and 0.1 mol/L, or between 0.01 mmol/L and 0.01 mol/L.

The zinc compound can be added at any stage during the activation procedure, in some embodiments it is added directly to the reactor. The zinc can be used as a mixed stock solution with the trialkylaluminium.

The non-metal oxygen containing additive can be used in any loading compared to the chromium such that the ratio of the molar amount of the non-metal oxygen containing additive to the molar amount of chromium in the source of chromium per $10^6$ g/g Cr productivity is between 0.01 and 400, or between 0.01 and 200, or between 0.01 and 100, or between 0.1 and 50, or between 0.1 and 20, or between 0.2 and 10.

The non-metal oxygen containing additive can be added at any stage during the reaction, and in some embodiments it is added directly to the reactor continuously during reaction. The amount of non-metal oxygen containing additive added can be varied during reaction. When gaseous, the non-metal oxygen containing additive can be used as a gas mixture with the olefinic compound if this is also a gas.

The process may also include combining one or more different sources of chromium with one or more different ligating compounds.

The oligomerisation catalyst or its individual components, in accordance with the invention, may also be immobilised by supporting it on a support material, for example, silica, alumina, $MgCl_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

The invention will now be described, by way of example only, with reference to the following non-limiting examples:

EXAMPLES

In each of the examples, one of the following representative reaction procedures was used, as will be evident from what follows.

Representative Procedure for Oligomerisation Reaction Using Borate or Aluminate Activator and Trialkylaluminium Co-Activator Under Batch Conditions:

A 300 mL or 1.2 L stainless steel reactor was heated to 120° C. under vacuum for 30 minutes, cooled to 60° C. and back-filled with Ar. The reactor was charged with solvent and if being used, charged with zinc compound.

Separately, TEA then activator salt (as stock solutions) were added sequentially to a stirred solution of chromium source and bis(diarylphosphanyl)amine ligand. The activation solution was added to the reactor and the reactor was pressurized to 50 bar with a gas mixture comprising ethylene containing the non-metal oxygen containing additive. The reaction pressure was kept constant through addition of ethylene monitored via a flow-meter. After cessation of ethylene uptake, the gas supply was closed and the reactor cooled to 0° C. Excess ethylene was bled and the reactor contents treated sequentially with 1000 μL of nonane (GC internal standard), MeOH and 10% HCl (aq). A sample of the organic phase was taken for GC-FID analysis. Any solid formed was collected, washed repeatedly with 10% HCl (aq.) and EtOH, dried overnight and weighed.

Representative Procedure for Oligomerisation Reaction Using Modified Methylaluminoxane Activator Under Batch Conditions:

A 300 mL or 1.2 L stainless steel reactor was heated to 120° C. under vacuum for 30 minutes, cooled to 60° C. and back-filled with Ar. The reactor was charged with solvent and if being used, charged with zinc compound.

Separately, modified methylaluminoxane (as a stock solution) was added to a stirred solution of chromium source and bis(diarylphosphanyl)amine ligand. The activation solution was added to the reactor and the reactor was pressurized to 50 bar with a gas mixture comprising ethylene containing the non-metal oxygen containing additive. The reaction pressure was kept constant through addition of ethylene/additive monitored via a flow-meter. After cessation of ethylene uptake, the gas supply was closed and the reactor cooled to 0° C. Excess ethylene was bled and the reactor contents treated sequentially with 1000 μL of nonane (GC internal standard), MeOH and 10% HCl (aq). A sample of the organic phase was taken for GC-FID analysis. Any solid formed was collected, washed repeatedly with 10% HCl (aq.) and EtOH, dried overnight and weighed.

Representative Procedure for Oligomerisation Reaction Under Continuous Operation Conditions:

A 5 or 300 L reactor system was initially started-up using a batch procedure analogous to that described above. Thereafter, the reactor was operated continuously via constant addition of activated catalyst solution and ethylene/additive feed. A continuous drain of the reactor was employed to ensure a stable fluid level within.

Example 1

Table 1 shows that when the triethylaluminium-tetrakis(perfluoro-tert-butoxy)aluminate oligomerisation catalyst is used, as the ratio of molar equivalents of non-metal oxygen containing additive (oxygen) to chromium per $10^6$ g/g Cr productivity (hereafter referred to as the "non-metal oxygen containing additive ratio" or "ratio") increases from 0.37 to 0.95 there is a ten-fold drop in polymer formation from 1.0 to 0.1 w %. As the ratio increases further from 0.95 the amount of polymer formed increases, but comparatively slowly, reaching 0.3 wt. % at an non-metal oxygen containing additive ratio of 6.72. This highlights an optimum in the non-metal oxygen containing additive ratio for polymer formation, which it is desirable to have minimized. Regarding activity, which it is desirable to maximize, this increases with non-metal oxygen containing additive ratio up to a maximum (see entry T1-3, non-metal oxygen containing additive ratio 2.86), before decreasing again.

Example 2

Table 2 highlights the same trends as Table 1 but at lower catalyst loading, the optimum performance in terms of both polymer formation and activity being at an non-metal oxygen containing additive ratio of 0.90 (entry T2-2).

Example 3

Table 3 shows data for the triethylaluminium-tetrakis(perfluorophenyl)borate catalyst, and was obtained from catalysis in a larger vessel that also allowed assessment of catalyst lifetime (productivity). The non-metal oxygen containing additive ratio is increased from 0.2 to 3.1, with a maximum in activity occurring between 0.6 and 2.8, and a minimum in polymer at 0.8. The maximum in catalyst lifetime occurs between non-metal oxygen containing additive ratios of 0.8 and 1.3.

Example 4

Table 4 shows optimization of the non-metal oxygen containing additive dosing as the chromium catalyst loading is lowered in a reactor of constant size. Entry T4-1 shows a 1.25 μmol run for comparison; for this run the productivity of 6M g/g Cr represents filling the autoclave. When the chromium catalyst loading is lowered to 0.5 μmol but the same level of oxygen dosed (0.33 ppm), the non-metal oxygen containing additive ratio is consequently increased, and activity drops and the catalyst fails to fill the autoclave (entry T4-2). By adjusting the oxygen dosing such that the non-metal oxygen containing additive ratio is decreased accordingly, activity and productivity are restored (T4-3), and further polymer formation is lowered. Entry T4-4 represents finer tuning of the non-metal oxygen containing additive ratio and benefits activity further. Entries T4-5 and T4-6 show another lowering of the chromium concentration and, comparing the two, the non-metal oxygen containing additive ratio is clearly more optimized in T4-5, as the activity and productivity are higher. A similar trend is observed for T4-7 and T4-8, the slightly higher non-metal oxygen containing additive ratio in T4-7 giving higher activity and productivity with lower polymer.

Example 5

Table 5 shows data for a bis(phosphanyl)amine ligand with ortho-alkyl-substituted phenyl rings at phosphorus. As the non-metal oxygen containing additive ratio is increased, activity and productivity increase, whilst polymer levels drop.

Example 6

Table 6 shows data for the methylaluminoxane catalyst system and illustrates that here also, an optimum non-metal oxygen containing additive ratio exists for productivity, activity and polymer, and that this ratio is very similar to that required for the triethylaluminium-tetrakis(perfluorophenyl)borate and triethylaluminium-tetrakis(perfluoro-tert-butoxy) aluminate catalysts. From an initial non-metal oxygen containing additive ratio of 0.4, a marked improvement occurs when this is increased to a range of 1.1 to 4.2, in all respects.

Example 7

Table 7 shows data for a different variant of the triethylaluminium-tetrakis(perfluorophenyl)borate catalyst, namely trioctylammonium tetrakis(perfluorophenyl)borate, and again reveals that the same trends hold true. Activity and productivity show maxima at a non-metal oxygen containing additive ratio of 1.2-1.3, whilst polymer, after showing a sharp drop (2.0 wt. % to 0.5 wt. %) when the non-metal oxygen containing additive ratio initially increases from 0.4 to 0.9, then shows a gradual decrease then increase, with a minima at an non-metal oxygen containing additive ratio of 3.2.

Example 8

Table 8 shows more data for the triethylaluminium-tetrakis(perfluorophenyl)borate and again shows a clear maximum in performance at an non-metal oxygen containing additive ratio of 1.1-1.2. Above or below this range activity and productivity both decrease, whilst polymer formation increases.

Example 9

Table 9 illustrates addition of the non-metal oxygen containing additive, in this case oxygen, using the same catalyst system as used in Example 8, directly to the reactor headspace as a pure component. As can be seen, a clear maximum again exists in terms of productivity and activity, whilst a minimum in polymer formation occurs at the same point.

Example 10

Table 10 illustrates addition of the non-metal oxygen containing additive, in this case nitrous oxide, using the same catalyst system as Example 8. It highlights that a clear maximum in terms of productivity and activity exists where the non-metal oxygen containing additive ratio is between 0.20-0.30, whilst polymer formation appears to steadily decrease as the non-metal oxygen containing additive ratio increases.

Example 11

Table 11 shows data for catalysis with dioxygen as the non-metal oxygen containing additive using a bis(phosphanyl)amine ligand with a cycloalkyl substituent at nitrogen. As the non-metal oxygen containing additive ratio is increased, activity increases then decreases, hence displaying a clear optimal maxima, whilst polymer levels drop.

Example 12

Table 12 shows data for catalysis with dioxygen as the non-metal oxygen containing additive using a bis(phosphanyl)amine ligand with an aryl substituent at nitrogen. As the non-metal oxygen containing additive ratio is increased, activity and productivity increase then decrease, hence displaying a clear optimal maxima, whilst polymer levels drop.

Example 13

Table 13 shows data for catalysis with dioxygen as the non-metal oxygen containing additive using a bis(phosphanyl)amine ligand with polar groups (specifically fluoro-substitution) at the ortho-position of the phenyl rings at phosphorus. As the non-metal oxygen containing additive ratio is increased, activity and productivity increase then decrease, hence displaying a clear optimal maxima, whilst polymer levels drop.

Example 14

Table 14 shows data for catalysis with dioxygen as the non-metal oxygen containing additive using a bis(phosphanyl)amine ligand with an alkenyl substituent at nitrogen. As the non-metal oxygen containing additive ratio is increased, activity and productivity increase then decrease, hence displaying a clear optimal maxima, whilst polymer levels drop then rise again, also showing a clear optimum.

Example 15

Table 15 shows data for catalysis with dioxygen as the non-metal oxygen containing additive using a bis(phosphanyl)amine ligand with an ether substituent at nitrogen. As the non-metal oxygen containing additive ratio is increased, activity and productivity increase then decrease, hence displaying a clear optimal maxima, whilst polymer levels drop then rise again, also showing a clear optimum.

Example 16

Table 16 shows data for catalysis with dioxygen as the non-metal oxygen containing additive using a N,N'-di(phosphanyl)hydrazine ligand. As the non-metal oxygen containing additive ratio is increased, activity and productivity increase then decrease, hence displaying a clear optimal maxima, whilst polymer levels drop.

Example 17

Table 17 shows data for catalysis with dioxygen as the non-metal oxygen containing additive using a bis(phosphanyl)amine ligand with polar groups (specifically methoxy-substitution) at the ortho-position of the phenyl rings at phosphorus. As the non-metal oxygen containing additive ratio is increased, activity and productivity increase then decrease, hence displaying a clear optimal maxima, whilst polymer levels stay constant initially, then increase once the maxima in activity has been passed.

Example 18

Table 18 shows data for catalysis with dioxygen as the non-metal oxygen containing additive using a P—N—P—N—H framework (as described in WO 2009/006979, WO 2009/068157, *Eur. J. Inorg. Chem.* 2010, 1167-1171 and *Chem. Eur. J.* 2011, 17, 6935-6938), specifically (diphenylphosphanyl)(phenyl(isopropylamino)phosphanyl)(isopropyl)amine in combination with tetraoctylammonium chloride and triethylaluminium. As the non-metal oxygen containing additive ratio is increased, activity and productivity increase to a maximum at a non-metal oxygen containing additive ratio of 36.2 then decrease. The polymer formation stays fairly constant until a non-metal oxygen containing additive ratio of 36.2 where it increases slightly, however once this point is passed the polymer formation increases further to 3.0 wt % at 398.9.

Example 19

Table 19 shows data for catalysis with dioxygen as the non-metal oxygen containing additive using a P—N—P—N—H framework (as described in WO 2009/006979, WO 2009/068157, *Eur. J. Inorg. Chem.* 2010, 1167-1171 and *Chem. Eur. J.* 2011, 17, 6935-6938), specifically (diphenylphosphanyl)(phenyl(isopropylamino)phosphanyl)(isopropyl)amine, but rather than activation as in Example 18, activated instead in combination with triethylaluminium and di(octadecyl)methylammonium tetrakis(perfluorophenyl)borate. As the non-metal oxygen containing additive ratio increases the activity and productivity again increase then decrease, whilst the polymer formation decreases then increases, demonstrating a clear optimum value.

Example 20

Table 20 shows data for the use of sulfur dioxide ($SO_2$) as the non-metal oxygen containing additive. It is observed that as the level of sulfur dioxide is steadily increased the activity and productivity reach a peak, then decrease, whilst polymer appears to generally decrease steadily in amount.

Example 21

Table 21 shows data for catalysis with dioxygen as the non-metal oxygen containing additive using a P—N—C=N ligand framework (as described in WO 2011/082192 A1 and *ACS Catal.*, 2012, 2, 2452-2455), specifically 1-(2,6-dimethylphenyl)-2-((4-methylphenyl)methylene)-3-(diphenylphosphanyl)-1,3-diaza-1-propene as a complex with chromium trichloride. The same trends are observed as with the other examples herein, namely that activity and productivity increase to a maximum then decrease again, whilst polymer decreases to a minimum then increases again, as the non-metal oxygen containing additive ratio steadily increases.

Example 22

Table 22 shows data from continuous mode operation of a chromium catalyst where the non-metal oxygen containing additive ratio is gradually decreased from 44.6 to 5.1. As can be seen a concomitant increase in activity and productivity occurs.

Examples 23 and 24

Tables 23 and 24 show continuous mode operation of a chromium catalyst under similar conditions to that of Example 11, but with a lower non-metal oxygen containing additive ratio (around 2.1 to 2.2), which gives better activity and productivity.

Example 25

Table 25 shows continuous mode operation of a chromium catalyst where the oxygen containing additive ratios started at zero, then increased stepwise to 0.2, 0.3 and 1.5, each time giving a stepwise improvement in activity and productivity.

Examples 26 and 27

Table 26 shows a similar run to that of Example 25, but with a stepwise increase starting from zero to 1.0, 2.6 and 4.2. As can be seen the maxima in terms of activity and productivity occurs at an non-metal oxygen containing additive ratio of 1.0, highlighting with Table 14 an optimum range of about 1.0 to 1.5 under these conditions. Table 27 also shows continuous mode operation data for a chromium catalyst and serves to further highlight the sensitivity of activity and productivity to the non-metal oxygen containing additive ratio, these parameters changing consistently in response to changes in the non-metal oxygen containing additive ratio.

These examples (1 to 27) illustrate the benefits of a non-metal oxygen containing additive upon catalysis when the non-metal oxygen containing additive is oxygen or nitrous oxide or sulfur dioxide.

These examples (1 to 27) illustrate the benefits of a non-metal oxygen containing additive upon catalysis with a range of PNP ligands, specifically bis(diphenylphosphanyl)(1-methylbutyl)amine, bis(diphenylphosphanyl)(1-methylheptyl)amine, bis(diphenylphosphanyl)(1,2-dimethylheptyl)amine, bis(diphenylphosphanyl)(1,2-dimethylpropyl)amine, bis(di(2-ethyl-phenyl)phosphanyl)(dodecyl)amine, bis(diphenylphosphanyl)(cyclohexyl)amine, bis(diphenylphosphanyl)(phenyl)amine, bis(diphenylphosphanyl)(3-isopropoxypropyl)amine, bis(diphenylphosphanyl)(3,7-dimethyl-2,6-octadienyl)amine, bis(di{orthomethoxyphenyl}phosphanyl)(methyl)amine and (di{orthofluorophenyl}phosphanyl)(diphenylphosphanyl)(isopropyl)amine. These ligands demonstrate a number of permutations of this ligand skeleton, specifically, n-alkyl, branched alkyl, cyclic alkyl, aryl, unsaturated hydrocarbyl (alkenyl) and ether groups at nitrogen, along with aromatic, alkyl substituted aromatic and polar substituted aromatic groups at phosphorus.

These examples (1 to 27) illustrate the benefits of a non-metal oxygen containing additive upon catalysis with a range of non-PNP ligands, specifically a hydrazine based ligand framework (P—N—N—P), a P—N—P—N—H framework (as described in WO 2009/006979, WO 2009/068157, Eur. J. Inorg. Chem. 2010, 1167-1171 and Chem. Eur. J. 2011, 17, 6935-6938) and a P—N—C=N framework (as described in WO 2011/082192 A1 and ACS Catal., 2012, 2, 2452-2455).

These examples (1 to 27) illustrate the benefits of a non-metal oxygen containing additive upon catalysis with a range of activator packages, specifically triethylaluminium-trityl tetrakis(perfluoro-tert-butoxy)aluminate, triethylaluminium dioctadecylmethylammonium tetrakis(perfluorophenyl)borate, triethylaluminium-trioctylammonium tetrakis(perfluorophenyl)borate, modified methylaluminoxane-3A and modified methylaluminoxane-20.

These examples (1 to 27) illustrate the benefits of a non-metal oxygen containing additive upon catalysis with a range of solvents, specifically cyclohexane, methylcyclohexane, chlorobenzene and 2,2,4-trimethylpentane.

These examples (1 to 27) illustrate the benefits of a non-metal oxygen containing additive upon catalysis under either batch or continuous operation conditions, from 150 mL up to 300 L volume reactor vessels.

These examples (1 to 27) illustrate the benefits of a non-metal oxygen containing additive upon catalysis with a range of chromium sources, specifically chromium(III) acetylacetonate, chromium(III)-2-ethylhexanoate and tris(2,2,6,6-tetramethyl-3,5-heptanedionato)chromium(III).

These examples (1 to 27) illustrate the benefits of a non-metal oxygen containing additive upon catalysis both with and without hydrogen ($H_2$) present.

These examples (1 to 27) illustrate the benefits of a non-metal oxygen containing additive upon catalysis both with and without dialkyl zinc present.

TABLE 1

Effect of dioxygen upon batch operation tetramerisation catalysis with a catalyst using triethylaluminium-tetrakis(perfluoro-tert-butoxy)aluminate and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ (10$^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T1-1 | 2.5 | 0.14 | 0.37 | 47.8 | 591,425 | 742,375 | 23.1 (83.1) | 65.9 (99.5) | 7.4 | 2.6 | 1.0 |
| T1-2 | 2.5 | 0.45 | 0.95 | 14.0 | 733,316 | 3,142,782 | 21.9 (81.2) | 66.1 (99.4) | 8.8 | 2.3 | 0.1 |
| T1-3 | 2.5 | 1.45 | 2.86 | 10.5 | 766,482 | 4,379,900 | 23.5 (82.1) | 64.6 (99.4) | 8.6 | 2.1 | 0.2 |
| T1-4 | 2.5 | 1.5 | 3.32 | 14.3 | 703,081 | 2,812,322 | 22.7 (82.4) | 66.0 (99.4) | 8.5 | 2.0 | 0.2 |
| T1-5 | 2.5 | 3.15 | 6.72 | 13.9 | 704,916 | 2,389,545 | 23.6 (83.0) | 65.4 (99.4) | 8.3 | 1.8 | 0.3 |
| T1-6 | 5.0 | 10.08 | 22.43 | 12.8 | 308,197 | 1,456,048 | 26.5 (85.6) | 62.5 (99.5) | 8.8 | 1.4 | 0.3 |

General conditions: Cr(acac)$_3$; 1.2 eq bis(diphenylphosphanyl)(1-methylbutyl)amine; 1.2 eq [Ph$_3$C][Al(O$^f$(Bu$^F$)$_4$]; 150 eq AlEt$_3$; 50 bar ethene; 60° C.; 70 mL PhCl; 300 mL autoclave.

TABLE 2

Effect of dioxygen upon batch operation tetramerisation catalysis with a catalyst using triethylaluminium-tetrakis(perfluoro-tert-butoxy)aluminate and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ (10$^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T2-1 | 1.25 | 0.33 | 0.71 | 10.3 | 1,407,796 | 6,497,519 | 23.7 (83.2) | 64.9 (99.4) | 8.2 | 2.4 | 0.5 |
| T2-2 | 1.25 | 0.45 | 0.90 | 10.8 | 1,446,885 | 6,677,931 | 22.5 (81.6) | 65.0 (99.4) | 8.8 | 2.9 | 0.3 |
| T2-3 | 1.25 | 1.45 | 3.64 | 13.3 | 1,191,758 | 4,673,562 | 22.1 (81.8) | 67.2 (99.5) | 7.4 | 2.5 | 0.5 |

General conditions: Cr($^t$Bu$_2$acac)$_3$; 1.2 eq bis(diphenylphosphanyl)(1-methylheptyl)amine; 1.2 eq [Ph$_3$C][Al(O$^f$(Bu$^F$)$_4$]; 150 eq AlEt$_3$; 50 bar ethene; 60° C.; 70 mL PhCl; 300 mL autoclave.

TABLE 3

Effect of dioxygen upon batch operation tetramerisation catalysis with a catalyst using triethylaluminium-tetrakis(perfluorophenyl)borate and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T3-1 | 1.25 | 0.06 | 0.2 | 218 | 1,360,772 | 4,898,778 | 20.8 (79.7) | 68.2 (99.2) | 7.8 | 2.3 | 2.1 |
| T3-2 | 1.25 | 0.10 | 0.3 | 112 | 3,062,700 | 5,717,040 | 21.4 (80.8) | 65.2 (99.2) | 9.9 | 2.7 | 0.9 |
| T3-3 | 1.25 | 0.16 | 0.4 | 95.1 | 3,812,730 | 6,043,177 | 20.1 (78.6) | 66.9 (99.2) | 9.9 | 2.1 | 0.7 |
| T3-4 | 1.25 | 0.26 | 0.6 | 80.9 | 4,842,694 | 6,529,565 | 21.3 (80.0) | 65.2 (98.7) | 10.4 | 2.3 | 0.6 |
| T3-5 | 1.25 | 0.35 | 0.8 | 73 | 5,126,774 | 6,237,576 | 22.3 (81.6) | 64.6 (99.2) | 10.2 | 2.1 | 0.3 |
| T3-6 | 1.25 | 0.56 | 1.3 | 65 | 5,596,370 | 6,062,734 | 20.9 (80.1) | 66.4 (99.2) | 10.2 | 1.9 | 0.4 |
| T3-7 | 1.25 | 1.22 | 2.8 | 119 | 3,492,790 | 6,927,368 | 20.9 (80.2) | 64.3 (99.1) | 12.1 | 2 | 0.8 |
| T3-8 | 1.25 | 1.25 | 3.1 | 165 | 2,293,597 | 6,307,390 | 21.0 (80.5) | 64.8 (99.2) | 11.5 | 2.3 | 1.2 |

General conditions: Cr($^t$Bu$_2$acac)$_3$; 1.2 eq bis(diphenylphosphanyl)(1-methylheptyl)amine; 1.2 eq [(C$_{18}$H$_{37}$)$_2$MeNH][B(C$_6$F$_5$)$_4$]; 420 eq AlEt$_3$; 50 bar ethene; 60° C.; 200 mL cyclohexane; 1.2 L rig.

TABLE 4

Effect of dioxygen upon batch operation tetramerisation catalysis with a catalyst using triethylaluminium-tetrakis(perfluorophenyl)borate and a PNP ligand with a branched alkyl substituent at nitrogen - addition of dioxygen entrained in the ethylene feed stream. Catalyst lifetime studies with varying amounts of Cr.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T4-1 | 1.25 | 0.33 | 0.77 | 75 | 6,544,292 | 5,214,575 | 21.3 (80.3) | 66.5 (99.4) | 9.4 | 2.0 | 0.6 |
| T4-2 | 0.5 | 0.33 | 1.13 | 168 | 6,610,651 | 2,360,947 | 23.3 (83.0) | 67.3 (99.5) | 7.1 | 1.6 | 0.4 |
| T4-3 | 0.5 | 0.22 | 0.44 | 254 | 14,765,518 | 3,489,291 | 22.1 (81.7) | 66.6 (99.5) | 8.9 | 1.6 | 0.2 |
| T4-4$^a$ | 0.61 | 0.22 | 0.53 | 161 | 12,344,531 | 4,609,035 | 21.9 (81.1) | 65.4 (99.1) | 10.1 | 1.7 | 0.4 |
| T4-5$^a$ | 0.3 | 0.18 | 0.34 | 443 | 15,553,564 | 2,105,152 | 20.5 (80.4) | 67.2 (99.2) | 9.8 | 1.8 | 0.2 |
| T4-6$^a$ | 0.22 | 0.18 | 0.72 | 368 | 10,066,616 | 1,640,850 | 20.9 (80.4) | 69.7 (99.3) | 7.2 | 1.4 | 0.2 |
| T4-7$^a$ | 0.15 | 0.16 | 0.61 | 411 | 10,957,498 | 1,598,079 | 20.9 (80.5) | 70.2 (99.3) | 6.7 | 1.4 | 0.1 |
| T4-8$^a$ | 0.15 | 0.14 | 0.71 | 414 | 6,138,542 | 889,000 | 21.7 (81.2) | 71.0 (99.3) | 5.3 | 1.1 | 0.5 |

General conditions: Cr($^t$Bu$_2$acac)$_3$; 1.2 eq bis(diphenylphosphanyl)(1-methylheptyl)amine; 7.4 eq [(C$_{18}$H$_{37}$)$_2$MeNH][B(C$_6$F$_5$)$_4$]; 420 eq AlEt$_3$; 50 bar ethene; 60° C.; 200 mL PhCl; 1.2 L autoclave.
$^a$200 mL 2,2,4-Trimethylpentane instead of PhCl.

TABLE 5

Effect of dioxygen upon batch operation tetramerisation catalysis with a catalyst using triethylaluminium-tetrakis(perfluorophenyl)borate catalyst and a PNP ligand with non-polar ortho-substituents on the phenyl rings at phosphorus and a linear alkyl (n-alkyl) substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T5-1 | 1.25 | 1.06 | 5.0 | 145 | 554,187 | 229,345 | 83.4 (99.2) | 14.9 (99.0) | 0.7 | 0.9 | 15.2 |
| T5-2 | 1.25 | 3.15 | 13.3 | 121 | 577,964 | 287,783 | 83.2 (99.3) | 14.7 (99.2) | 1.4 | 0.6 | 14.8 |
| T5-3 | 1.25 | 8.53 | 36.3 | 118 | 588,135 | 297,874 | 82.9 (99.2) | 14.8 (99.2) | 1.4 | 0.7 | 10.5 |

General conditions: Cr(2-EH)$_3$; 1.2 eq bis(di(2-ethyl-phenyl)phosphanyl)(dodecyl)amine; 7.4 eq [(C$_{18}$H$_{37}$)$_2$MeNH][B(C$_6$F$_5$)$_4$]; 50 eq ZnEt$_2$; 50 bar ethene; 60° C.; 70 mL cyclohexane, 300 mL autoclave.

TABLE 6

Effect of dioxygen upon batch operation tetramerisation catalysis with a catalyst using methylaluminoxane and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T6-1 | 2.5 | 0.15 | 0.4 | 77 | 738,499 | 575,454 | 27.2 (86.4) | 60.9 (99.5) | 8.5 | 1.0 | 1.7 |
| T6-2 | 2.5 | 0.15 | 0.5 | 45 | 509,733 | 679,644 | 25.5 (86.3) | 63.6 (99.5) | 8.4 | 1.1 | 1.0 |

TABLE 6-continued

Effect of dioxygen upon batch operation tetramerisation catalysis with a catalyst using methylaluminoxane and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T6-3 | 2.5 | 0.45 | 1.1 | 35 | 788,236 | 1,351,263 | 24.9 (86.1) | 62.9 (99.6) | 10.2 | 1.0 | 0.7 |
| T6-4 | 2.5 | 0.45 | 1.2 | 37 | 771,398 | 1,266,317 | 25.3 (86.1) | 63.1 (99.5) | 9.6 | 1.0 | 0.7 |
| T6-5 | 2.5 | 0.45 | 1.2 | 33 | 759,381 | 1,387,701 | 26.1 (87.0) | 62.4 (99.5) | 9.1 | 0.9 | 0.4 |
| T6-6 | 2.5 | 0.45 | 1.2 | 36 | 741,202 | 1,245,136 | 27.0 (87.6) | 61.2 (99.5) | 10.0 | 0.9 | 0.5 |
| T6-7 | 2.5 | 1.45 | 4.2 | 29 | 707,819 | 1,464,452 | 26.1 (87.0) | 62.9 99.5) | 8.8 | 0.9 | 0.3 |

General conditions: Cr(acac)$_3$; 1.2 eq bis(diphenylphosphanyl)(1,2-dimethylpropyl)amine; 480 eq modified methylaluminoxane-3A; 45 bar ethene; 60° C.; 100 mL 2,2,4-trimethylpentane, 450 mL autoclave.

TABLE 7

Effect of dioxygen upon batch operation tetramerisation catalysis with a catalyst using triethylaluminium-tetrakis(perfluorophenyl)borate where the ammonium cation is trioctylammonium - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T7-1 | 1.25 | 0.14 | 0.4 | 140 | 1,906,978 | 817,276 | 32.1 (89.9) | 59.7 (99.6) | 7.1 | 0.8 | 2.0 |
| T7-2 | 1.25 | 0.4 | 0.9 | 210 | 4,821,373 | 1,380,383 | 33.5 (90.9) | 55.6 (99.5) | 10.0 | 0.7 | 0.5 |
| T7-3 | 1.25 | 0.5 | 1.2 | 155 | 5,518,510 | 2,137,806 | 34.3 (91.2) | 53.7 (99.5) | 11.0 | 0.7 | 0.4 |
| T7-4 | 1.25 | 0.6 | 1.3 | 113 | 4,432,616 | 2,354,491 | 34.9 (91.6) | 53.7 (99.6) | 10.6 | 0.6 | 0.3 |
| T7-5 | 1.25 | 1.3 | 3.2 | 132 | 3,331,635 | 1,518,021 | 35.0 (91.4) | 54.1 (99.6) | 10.1 | 0.6 | 0.2 |
| T7-6 | 1.25 | 4.1 | 34.9 | 73 | 312,974 | 258,775 | 37.3 (41.3) | 57.2 (99.3) | 4.5 | 0.7 | 0.4 |
| T7-7 | 1.25 | 9.3 | 55.3 | 137 | 380,359 | 166,763 | 41.3 (92.8) | 52.6 (99.4) | 4.9 | 0.9 | 0.8 |

General conditions: Cr(2-EH)$_3$; 1.2 eq bis(diphenylphosphanyl)(1,2-dimethylheptyl)amine; 1.2 eq [Oct$_3$NH][B(C$_6$F$_5$)$_4$]; 420 eq AlEt$_3$; 100 eq ZnEt$_2$; 50 bar ethene; 60° C.; 200 mL methylcyclohexane, 1.2 L autoclave.

TABLE 8

Effect of dioxygen upon batch operation tetramerisation catalysis with a catalyst using triethylaluminium-tetrakis(perfluorophenyl)borate and a PNP ligand with a branched alkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T8-1 | 1.25 | 0.4 | 1.0 | 109 | 5,599,228 | 3,100,157 | 33.4 (90.9) | 55.2 (99.5) | 10.4 | 0.8 | 0.6 |
| T8-2 | 1.25 | 0.5 | 1.1 | 78 | 5,533,686 | 4,274,951 | 34.7 (91.5) | 53.9 (99.5) | 10.5 | 0.7 | 0.3 |
| T8-3 | 1.25 | 0.5 | 1.2 | 83 | 5,600,545 | 4,048,586 | 34.4 (91.4) | 53.4 (99.5) | 11.2 | 0.7 | 0.3 |
| T8-4 | 1.25 | 0.9 | 1.9 | 93 | 4,909,993 | 3,190,609 | 35.6 (91.9) | 52.7 (99.5) | 10.9 | 0.6 | 0.4 |

General conditions: Cr(2-EH)$_3$; 1.2 eq bis(diphenylphosphanyl)(1,2-dimethylheptyl)amine; 1.2 eq [(C$_{18}$H$_{37}$)$_2$MeNH][B(C$_6$F$_5$)$_4$] 420 eq AlEt$_3$; 100 eq ZnEt$_2$; 50 bar ethene; 60° C.; 200 mL methylcyclohexane, 1.2 L autoclave.

TABLE 9

Effect of dioxygen upon batch operation tetramerisation catalysis with the triethylaluminium-tetrakis(perfluorophenyl)borate catalyst - addition of pure dioxygen gas to reactor headspace. Pure oxygen gas was injected into the reactor headspace via syringe.

| Entry | Cr {μmol} | $O_2$ addition {cm$^3$} | (mol $O_2$) (mol Cr)$^{-1}$ ($10^6$ Prod)$^{-1}$ | Productivity {g/gCr} | Activity {g/gCr/h} | $C_6$ (1-$C_6$) (wt %) | $C_8$ (1-$C_8$) {wt %} | $C_{10-15}$ {wt %} | PE {wt %} |
|---|---|---|---|---|---|---|---|---|---|
| T9-1 | 2.5 | 0 | 0 | 255,478 | 412,779 | 30.4 (91.9) | 53.1 (99.6) | 6.0 | 10.2 |
| T9-2 | 2.5 | 0.5 | 8.6 | 962,377 | 4,914,265 | 33.3 (90.7) | 56.7 (99.5) | 9.5 | 0.3 |
| T9-3 | 2.5 | 0.5 | 8.8 | 943,331 | 4,851,417 | 33.3 (91.0) | 57.1 (99.5) | 8.8 | 0.6 |
| T9-4 | 2.5 | 3.0 | 170.6 | 292,632 | 877,896 | 40.7 (95.4) | 40.1 (99.7) | 5.0 | 14.3 |

General conditions: Cr(acac)$_3$; 1.2 eq bis(diphenylphosphanyl)(isopropyl)amine; 2.4 eq [Ph$_3$C][B(Ph$^F$)$_4$]; 150 eq AlEt$_3$; 50 bar ethene; 60° C.; 100 mL PhCl; 450 mL autoclave.

TABLE 10

Effect of nitrous oxide (N₂O) upon batch operation tetramerisation catalysis with the triethylaluminium-tetrakis(perfluorophenyl)borate catalyst - addition of nitrous oxide (N₂O) entrained in the ethylene feed stream.

| Entry | Cr {μmol} | $N_2O$ in ethene {ppm} | (mol $N_2O$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T10-1 | 1.25 | 0.16 | 0.23 | 147 | 6,199,021 | 2,534,811 | 31.7 (90.4) | 56.5 (99.3) | 10.5 | 1.0 | 1.10 |
| T10-2 | 1.25 | 0.21 | 0.30 | 94 | 6,040,887 | 3,840,903 | 32.5 (90.8) | 55.7 (99.3) | 10.7 | 0.9 | 0.52 |
| T10-3 | 1.25 | 0.25 | 0.42 | 100 | 6,112,754 | 3,653,040 | 32.5 (90.9) | 55.3 (99.5) | 11.0 | 1.0 | 0.32 |
| T10-4 | 1.25 | 0.61 | 0.97 | 125 | 6,852,202 | 3,279,437 | 33.2 (91.4) | 51.3 (99.5) | 13.9 | 1.4 | 0.24 |
| T10-5 | 1.25 | 1.32 | 2.28 | 122 | 5,728,907 | 2,817,495 | 36.3 (92.4) | 47.3 (99.4) | 14.8 | 1.4 | 0.26 |
| T10-6 | 1.25 | 4.48 | 7.01 | 80 | 2,710,966 | 2,041,732 | 37.8 (92.9) | 47.4 (99.4) | 13.6 | 1.0 | 0.14 |
| T10-7 | 1.25 | 9.80 | 17.9 | 70 | 1,522,024 | 1,310,208 | 45.1 (94.2) | 43.1 (99.3) | 10.7 | 1.0 | 0.08 |
| T10-8 | 1.25 | 24.90 | 40.5 | 61 | 719,201 | 706,253 | 47.7 (94.6) | 42.1 (99.0) | 9.6 | 0.3 | 0.06 |

General conditions: Cr(2-EH)₃; 1.2 eq bis(diphenylphosphanyl)(1,2-dimethylheptyl)amine; 1.2 eq[($C_{18}H_{37}$)₂MeNH][B($C_6F_5$)₄]; 420 eq AlEt₃; 100 eq ZnEt₂; 50 bar ethene; 60° C.; 200 mL methylcyclohexane; 1.2 L autoclave.

TABLE 11

Effect of dioxygen upon batch operation tetramerisation catalysis with a catalyst using triethylaluminium-tetrakis(perfluorophenyl)borate catalyst and a PNP ligand with a cycloalkyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T11-1 | 1.25 | 0.14 | 0.4 | 142 | 3,257,163 | 1,357,943 | 22.9 (82.0) | 66.0 (99.2) | 8.9 | 1.8 | 1.4 |
| T11-2 | 1.25 | 0.82 | 2.4 | 48 | 2,759,863 | 3,483,698 | 23 (81.7) | 65.8 (99.0) | 8.7 | 2.0 | 0.5 |
| T11-3 | 1.25 | 9.1 | 37.3 | 155 | 1,158,509 | 448,070 | 24.3 (82.9) | 67.9 (99.3) | 6.2 | 1.1 | 0.5 |

General conditions: Cr(2-EH)₃; 1.2 eq bis(diphenylphosphanyl)(cyclohexyl)amine; 1.2 eq [($C_{18}H_{37}$)₂MeNH][B($C_6F_5$)₄]; 420 eq AlEt₃; 100 eq ZnEt₂; 45 bar ethene; 60° C.; 200 mL methylcyclohexane, 1.2 L autoclave.

TABLE 12

Effect of dioxygen upon batch operation tetramerisation catalysis with a catalyst using triethylaluminium-tetrakis(perfluorophenyl)borate catalyst and a PNP ligand with an aryl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T12-1 | 1.25 | 0.14 | 0.6 | 242.6 | 1,878,783 | 464,662 | 24.6 (65.2) | 63.2 (97.6) | 6.8 | 2.7 | 10.9 |
| T12-2 | 1.25 | 1.2 | 3.0 | 122.6 | 2,791,757 | 1,366,648 | 24.4 (64.5) | 62.9 (97.5) | 8.9 | 2.4 | 1.9 |
| T12-3 | 1.25 | 9.7 | 65.0 | 59.3 | 573,392 | 580,487 | 25.8 (65.7) | 66.1 (97.8) | 4.7 | 2.0 | 0.7 |

General conditions: Cr(2-EH)₃; 1.2 eq bis(diphenylphosphanyl)(phenyl)amine; 1.2 eq [($C_{18}H_{37}$)₂MeNH][B($C_6F_5$)₄]; 420 eq AlEt₃; 100 eq ZnEt₂; 45 bar ethene; 60° C.; 200 mL methylcyclohexane, 1.2 L autoclave.

TABLE 13

Effect of dioxygen upon batch operation tetramerisation catalysis with a catalyst using a PNP ligand with ortho-substituted phenyl rings and triethylaluminium-tetrakis(perfluorophenyl)borate catalyst - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T13-1 | 1.25 | 0.14 | 0.4 | 165 | 2,315,928 | 843,690 | 19.1 (91.5) | 68.3 (99.4) | 7.7 | 4.5 | 4.9 |
| T13-2 | 1.25 | 0.87 | 2.3 | 46 | 2,860,016 | 3,760,430 | 17.9 (90.8) | 68.5 (99.2) | 8.3 | 5.0 | 1.4 |
| T13-3 | 1.25 | 7.2 | 30.1 | 266 | 1,871,641 | 422,970 | 20.6 (92.0) | 68.0 (99.3) | 7.4 | 3.7 | 1.0 |

General conditions: Cr(2-EH)₃; 1.2 eq (di{ortho-fluorophenyl}phosphanyl)(diphenylphosphanyl)(isopropyl)amine; 1.2 eq [($C_{18}H_{37}$)₂MeNH][B($C_6F_5$)₄]; 420 eq AlEt₃; 100 eq ZnEt₂; 45 bar ethene; 60° C.; 200 mL methylcyclohexane, 1.2 L autoclave.

TABLE 14

Effect of dioxygen upon batch operation tetramerisation catalysis with a catalyst using triethylaluminium-tetrakis(perfluorophenyl)borate catalyst and a PNP ligand with an alkenyl substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T14-1 | 1.25 | 0.14 | 0.5 | 205 | 2,326,418 | 681,568 | 22.3 (45.2) | 62.2 (96.2) | 7.1 | 6.0 | 5.1 |
| T14-2 | 1.25 | 0.92 | 2.3 | 75 | 2,641,089 | 2,105,386 | 22.8 (46.5) | 62.1 (96.3) | 8.6 | 4.1 | 0.4 |
| T14-3 | 1.25 | 7.5 | 46.2 | 147 | 750,022 | 306,618 | 23.5 (48.7) | 63.9 (96.6) | 6.2 | 4.3 | 0.6 |

General conditions: Cr(2-EH)$_3$; 1.2 eq bis(diphenylphosphanyl)(3,7-dimethyl-2,6-octadienyl)amine; 1.2 eq [(C$_{18}$H$_{37}$)$_2$MeNH][B(C$_6$F$_5$)$_4$]; 420 eq AlEt$_3$; 100 eq ZnEt$_2$; 45 bar ethene; 60° C.; 200 mL methylcyclohexane, 1.2 L autoclave.

TABLE 15

Effect of dioxygen upon batch operation tetramerisation catalysis with a catalyst using triethylaluminium-tetrakis(perfluorophenyl)borate and a PNP ligand with an ether substituent at nitrogen - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T15-1 | 1.25 | 0.14 | 0.5 | 163 | 2,314,421 | 850,369 | 20.2 (49.2) | 64.9 (96.9) | 8.1 | 5.1 | 3.3 |
| T15-2 | 1.25 | 0.78 | 2.4 | 82 | 2,487,791 | 1,814,484 | 20.9 (51.7) | 65.3 (97.1) | 8.5 | 3.3 | 0.2 |
| T15-3 | 1.25 | 8.8 | 116.5 | 45 | 237,311 | 316,181 | 21.6 (54.6) | 69.3 (97.4) | 4.5 | 3.1 | 0.3 |

General conditions: Cr(2-EH)$_3$; 1.2 eq bis(diphenylphosphanyl)(3-isopropoxypropyl)amine; 1.2 eq [(C$_{18}$H$_{37}$)$_2$MeNH][B(C$_6$F$_5$)$_4$]; 420 eq AlEt$_3$; 100 eq ZnEt$_2$; 45 bar ethene; 60° C.; 200 mL methylcyclohexane, 1.2 L autoclave.

TABLE 16

Effect of dioxygen upon batch operation tetramerisation catalysis with a catalyst using triethylaluminium-tetrakis(perfluorophenyl)borate and a hydrazine framework P^P ligand - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T16-1 | 1.25 | 0.14 | 1.4 | 138 | 432,020 | 187,428 | 59.9 (96.6) | 30.6 (99.2) | 4.1 | 2.8 | 29.6 |
| T16-2 | 1.25 | 0.71 | 6.3 | 71 | 643,970 | 548,319 | 63.8 (96.6) | 31.2 (99.4) | 4.3 | 0.6 | 1.7 |
| T16-3 | 1.25 | 8.9 | 193.1 | 41 | 131,643 | 194,068 | 63.7 (96.3) | 32.0 (99.1) | 3.4 | 0.6 | 1.0 |

General conditions: Cr(2-EH)$_3$; 1.2 eq N-methyl-N-(diphenylphosphanyl)-N'-isopentyl-N'-(diphenylphosphanyl)hydrazine; 1.2 eq [(C$_{18}$H$_{37}$)$_2$MeNH][B(C$_6$F$_5$)$_4$]; 420 eq AlEt$_3$; 100 eq ZnEt$_2$; 45 bar ethene; 60° C.; 200 mL methylcyclohexane, 1.2 L autoclave.

TABLE 17

Effect of dioxygen upon batch operation tetramerisation catalysis with a catalyst using a PNP ligand with ortho-substituted phenyl rings and MMAO co-catalyst - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T17-1 | 1.25 | 0.14 | 0.4 | 44 | 2,424,662 | 3,336,691 | 84.6 (99.7) | 8.9 (99.9) | 6.5 | 0.0 | 0.4 |
| T17-2 | 1.25 | 0.33 | 1.0 | 21 | 2,472,884 | 7,179,339 | 84.7 (99.7) | 9.4 (99.8) | 5.8 | 0.0 | 0.4 |
| T17-3 | 1.25 | 9.4 | 29.6 | 77 | 2,389,169 | 1,851,271 | 86.8 (99.6) | 7.6 (99.6) | 5.6 | 0.0 | 0.8 |

General conditions: Cr(2-EH)$_3$; 1.2 eq bis(di{ortho-methoxyphenyl}phosphanyl)(methyl)amine; 1882 eq modified methylaluminoxane-20; 45 bar ethene; 60° C.; 200 mL methylcyclohexane, 1.2 L autoclave.

TABLE 18

Effect of dioxygen upon batch operation tetramerisation catalysis with a catalyst using a PNPN(H) ligand (as described in WO 2009/006979, WO 2009/068157, *Eur. J. Inorg. Chem.* 2010, 1167-1171 and *Chem. Eur. J.* 2011, 17, 6935-6938), and ammonium halide additive and triethylaluminium - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T18-1 | 10 | 0.14 | 0.5 | 71 | 51,227 | 43,598 | 93.7 (99.2) | 0.3 (61.1) | 5.1 | 0.0 | 0.4 |
| T18-2 | 10 | 0.90 | 5.7 | 71 | 52,670 | 44,746 | 94.2 (99.2) | 0.3 (51.0) | 5.2 | 0.0 | 0.4 |

TABLE 18-continued

Effect of dioxygen upon batch operation tetramerisation catalysis with a catalyst using a PNPN(H) ligand (as described in WO 2009/006979, WO 2009/068157, *Eur. J. Inorg. Chem.* 2010, 1167-1171 and *Chem. Eur. J.* 2011, 17, 6935-6938), and ammonium halide additive and triethylaluminium - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T18-3 | 10 | 9.2  | 24.0  | 72 | 68,712 | 57,633 | 94.5 (99.2) | 0.2 (71.3)  | 5.0 | 0.0 | 0.4 |
| T18-4 | 10 | 17.2 | 36.2  | 73 | 85,826 | 70,477 | 94.5 (99.2) | 0.2 (100.0) | 4.9 | 0.0 | 0.8 |
| T18-5 | 10 | 44.9 | 398.9 | 70 | 13,604 | 11,661 | 92.2 (99.2) | 1.4 (20.7)  | 6.1 | 0.0 | 3.0 |

General conditions: Cr(acac)$_3$; 1.75 eq (diphenylphosphanyl)(phenyl(isopropylamino)phosphanyl)(isopropyl)amine; 5 eq [(C$_8$H$_{17}$)$_4$N][Cl]; 25 eq AlEt$_3$; 33 bar ethene; 52° C.; 200 mL chlorobenzene, 1.2 L autoclave.

TABLE 19

Effect of dioxygen upon batch operation tetramerisation catalysis with a catalyst using a PNPN(H) ligand and triethylaluminium-tetrakis(perfluorophenyl)borate - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T19-1 | 2.5 | 0.9  | 5.5   | 70 | 146,293 | 125,037 | 42.1 (92.1) | 53.9 (99.5) | 3.2 | 0.6 | 3.4 |
| T19-2 | 2.5 | 9.1  | 113.7 | 74 | 135,704 | 110,129 | 42.1 (92.0) | 54.0 (99.2) | 3.1 | 0.5 | 4.9 |
| T19-3 | 2.5 | 22.2 | 260.9 | 69 | 171,126 | 148,019 | 41.0 (91.8) | 55.6 (99.3) | 3.0 | 0.2 | 2.2 |

General conditions: Cr(2-EH)$_3$; 1.2 eq (diphenylphosphanyl)(phenyl(isopropylamino)phosphanyl)(isopropyl)amine; 1.2 eq [(C$_{18}$H$_{37}$)$_2$MeNH][B(C$_6$F$_5$)$_4$]; 420 eq AlEt$_3$; 100 eq ZnEt$_2$; 45 bar ethene; 60° C.; 200 mL methylcyclohexane, 1.2 L autoclave.

TABLE 20

Effect of sulphur dioxide ($SO_2$) upon batch operation tetramerisation catalysis with the triethylaluminium-tetrakis(perfluorophenyl)borate catalyst - addition of sulphur dioxide ($SO_2$) entrained in the ethylene feed stream.

| Entry | Cr {μmol} | $SO_2$ in ethene {ppm} | (mol $SO_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T20-1 | 1.25 | 0    | 0     | 253 | 4,102,244 | 971,456   | 22.8 (81.5) | 66.7 (99.1) | 8.4 | 1.6 | 2.9 |
| T20-2 | 1.25 | 0.75 | 0.87  | 209 | 4,552,126 | 1,309,336 | 23.6 (81.8) | 65.8 (99.2) | 8.4 | 1.6 | 2.8 |
| T20-3 | 1.25 | 1.0  | 1.16  | 177 | 4,287,715 | 1,451,276 | 23.4 (81.8) | 65.5 (99.1) | 8.9 | 1.6 | 2.5 |
| T20-4 | 1.25 | 2.0  | 6.2   | 204 | 2,782,874 | 819,966   | 23.3 (81.6) | 67.0 (99.2) | 7.5 | 1.6 | 1.1 |
| T20-5 | 1.25 | 4.5  | 27.6  | 138 | 783,763   | 340,520   | 22.9 (81.3) | 69.3 (99.2) | 5.0 | 2.3 | 2.3 |
| T20-6 | 1.25 | 9.1  | 87.4  | 74  | 395,121   | 322,256   | 24.3 (82.5) | 69.1 (99.2) | 4.2 | 1.9 | 1.6 |

General conditions: Cr(2-EH)$_3$; 1.2 eq bis(diphenylphosphanyl)(1-methylheptyl)amine; 1.2 eq [(C$_{18}$H$_{37}$)$_2$MeNH][B(C$_6$F$_5$)$_4$]; 420 eq AlEt$_3$; 100 eq ZnEt$_2$; 50 bar ethene; 60° C.; 200 mL methylcyclohexane, 1.2 L autoclave.

TABLE 21

Effect of dioxygen upon batch operation tetramerisation catalysis with a catalyst using a P—N—C═N ligand framework (as described in WO 2011/082192 A1 and *ACS Catal.*, 2012, 2, 2452-2455) - addition of dioxygen entrained in the ethylene feed stream.

| Entry | Cr {μmol} | $O_2$ in ethene {ppm} | (mol $O_2$) (mol Cr)$^{-1}$ ($10^6$ Prod)$^{-1}$ | Rxn Time {min} | Productivity {g/gCr} | Activity {g/gCr/h} | $C_6$ (1-$C_6$) {wt %} | $C_8$ (1-$C_8$) {wt %} | $C_{10-14}$ {wt %} | $C_{15+}$ {wt %} | PE {wt %} |
|---|---|---|---|---|---|---|---|---|---|---|---|
| T21-1 | 1.25 | 0.14 | 2.5  | 41 | 45,182  | 66,847  | 63.3 (98.8) | 34.5 (97.6) | 1.1 | 0.4 | 63.5 |
| T21-2 | 1.25 | 0.25 | 3.4  | 30 | 149,613 | 297,984 | 65.5 (97.4) | 32.3 (99.3) | 1.8 | 0.2 | 6.2  |
| T21-3 | 1.25 | 3.1  | 23.7 | 32 | 131,556 | 245,932 | 66.7 (99.7) | 31.0 (99.2) | 1.6 | 0.3 | 19.9 |

General conditions: (Ph$_2$P—N{H}—C[CH$_2$—{4—Me—C$_6$H$_4$}]═N{2,6-Me$_2$—C$_6$H$_3$})CrCl$_3$; 800 eq modified methylaluminoxane-20; 50 bar ethene; 1 bar H$_2$; 60° C.; 65 mL methylcyclohexane, 250 mL autoclave.

TABLE 22

Effect of dioxygen upon continuous operation tetramerisation catalysis with the triethylaluminium-tetrakis(perfluorophenyl)borate catalyst - addition of dioxygen entrained in the ethylene feed stream.

| Time {min} | $O_2$ in ethene {ppm} | Reactor liquid volume {mL} | Productivity {g/gCr} | Activity {g/gCr/h} | (mol $O_2$) (mol Cr)$^{-1}$ ($10^6$ Prod)$^{-1}$ |
|---|---|---|---|---|---|
| 140 | 25.0 | 2500 | 699,851 | 704,794 | 44.6 |
| 160 | 18.0 | 2500 | 676,861 | 655,803 | 29.7 |
| 180 | 18.0 | 2500 | 855,883 | 848,279 | 29.1 |
| 200 | 16.0 | 2500 | 851,496 | 758,706 | 29.3 |
| 220 | 12.0 | 2500 | 977,091 | 1,025,719 | 18.8 |
| 240 | 11.5 | 2500 | 1,040,392 | 1,167,585 | 18.5 |
| 260 | 10.4 | 2500 | 1,233,240 | 1,371,631 | 14.3 |
| 280 | 9.6 | 2600 | 1,460,823 | 1,624,056 | 13.6 |
| 300 | 10.3 | 2700 | 1,479,391 | 1,473,937 | 9.7 |
| 320 | 11.1 | 2800 | 1,338,102 | 1,186,923 | 13.0 |
| 340 | 8.7 | 2900 | 991,519 | 699,583 | 13.7 |
| 360 | 7.8 | 3000 | 1,340,126 | 1,619,904 | 14.8 |
| 380 | 8.5 | 2650 | 1,599,314 | 1,666,747 | 10.0 |
| 400 | 7.2 | 2650 | 2,314,118 | 2,642,525 | 6.9 |
| 420 | 6.9 | 2650 | 2,074,151 | 1,958,512 | 8.3 |
| 440 | 6.7 | 2650 | 2,218,386 | 2,371,429 | 9.5 |
| 460 | 6.0 | 2650 | 1,795,378 | 1,780,391 | 6.5 |
| 480 | 6.6 | 2650 | 1,721,843 | 1,728,861 | 6.7 |
| 500 | 5.9 | 2650 | 2,450,666 | 4,721,176 | 5.1 |

General conditions: Cr(2-EH)$_3$; 1.2 eq bis(diphenylphosphanyl)(1,2-dimethylheptyl) amine; 1.2 eq [(C$_{18}$H$_{37}$)$_2$MeNH][B(C$_6$F$_5$)$_4$]; 800 eq AlEt$_3$; 100 eq ZnEt$_2$; 40 bar ethene; 60° C.; 5 L autoclave.
Average selectivity for run 36.6 (91.8), 56.4(99.5), 7.3, 0.2, 0.5 [C$_6$(1-C$_6$), C$_8$(1-C$_8$), C$_{10-14}$, C$_{15+}$, PE].

TABLE 23

Effect of dioxygen upon continuous operation tetramerisation catalysis with the triethylaluminium-tetrakis(perfluorophenyl)borate catalyst - addition of dioxygen entrained in the ethylene feed stream.

| Time {min} | $O_2$ in ethene {ppm} | Reactor liquid volume {mL} | Productivity {g/gCr} | Activity {g/gCr/h} | (mol $O_2$) (mol Cr)$^{-1}$ ($10^6$ Prod)$^{-1}$ |
|---|---|---|---|---|---|
| 180 | 1.7 | 2500 | 1,020,023 | 1,045,137 | 2.5 |
| 200 | 1.4 | 2500 | 1,199,080 | 1,245,544 | 1.8 |
| 220 | 2.1 | 2500 | 1,382,399 | 1,253,289 | 2.5 |
| 240 | 1.9 | 3000 | 1,397,523 | 1,281,556 | 2.1 |
| 260 | 1.5 | 2500 | 1,636,382 | 1,518,487 | 2.0 |
| 280 | 1.4 | 3000 | 1,492,401 | 1,412,282 | 1.0 |
| 300 | 1.6 | 2500 | 1,757,314 | 1,614,933 | 2.3 |
| 320 | 1.9 | 2500 | 1,736,097 | 1,959,001 | 1.9 |
| 340 | 1.9 | 2500 | 2,055,220 | 2,291,631 | 1.8 |
| 360 | 2.0 | 2500 | 1,897,734 | 2,087,688 | 2.2 |
| 380 | 1.3 | 2500 | 2,071,900 | 2,110,335 | 1.9 |
| 400 | 1.6 | 2500 | 1,760,878 | 1,769,223 | 1.3 |
| 420 | 1.6 | 2500 | 1,619,919 | 1,550,895 | 1.9 |
| 440 | 1.5 | 2500 | 1,615,235 | 1,528,507 | 2.1 |
| 460 | 1.5 | 2500 | 1,863,409 | 2,210,046 | 1.6 |
| 480 | 1.5 | 2500 | 2,039,614 | 2,137,915 | 1.4 |
| 500 | 1.6 | 2500 | 1,535,017 | 1,621,403 | 1.8 |
| 520 | 2.1 | 2500 | 1,597,738 | 1,188,548 | 3.4 |
| 540 | 1.5 | 2500 | 1,265,682 | 1,423,778 | 2.0 |
| 560 | 2.0 | 2500 | 1,270,991 | 1,101,654 | 2.6 |
| 580 | 1.9 | 2500 | 752,448 | 651,260 | 3.3 |
| 600 | 1.8 | 2500 | 574,617 | 389,549 | 4.9 |
| 620 | 1.6 | 2500 | 1,126,394 | 1,033,028 | 3.2 |
| 640 | 2.4 | 2500 | 1,583,374 | 1,832,963 | 3.5 |
| 660 | 3.1 | 2500 | 2,063,667 | 2,281,934 | 4.5 |
| 680 | 1.7 | 2500 | 1,722,593 | 1,860,883 | 1.8 |
| 702 | 1.9 | 2500 | 1,747,949 | 1,762,639 | 3.1 |
| 721 | 2.0 | 2500 | 1,950,184 | 2,026,401 | 1.9 |
| 741 | 1.8 | 2500 | 1,994,934 | 2,292,685 | 1.7 |
| 761 | 1.6 | 2500 | 1,871,385 | 1,955,962 | 1.6 |
| 781 | 1.4 | 2500 | 1,431,389 | 1,419,257 | 1.7 |
| 801 | 1.6 | 2500 | 1,693,598 | 1,381,623 | 1.6 |
| 821 | 1.1 | 2500 | 1,555,228 | 1,260,629 | 1.2 |
| 841 | 1.7 | 2500 | 1,673,081 | 1,305,192 | 1.8 |
| 861 | 1.5 | 2500 | 1,493,250 | 1,543,494 | 2.2 |
| 881 | 1.1 | 2500 | 1,697,416 | 1,689,066 | 1.3 |
| 901 | 1.8 | 2500 | 1,772,457 | 1,738,452 | 2.4 |
| 921 | 1.2 | 2500 | 1,735,214 | 1,687,755 | 1.8 |
| 944 | 2.1 | 2500 | 1,972,191 | 2,263,634 | 3.5 |
| Average | 1.7 | — | 1,605,794 | 1,608,417 | 2.2 |

General conditions: Cr(2-EH)$_3$; 1.2 eq bis(diphenylphosphanyl)(1,2-dimethylheptyl) amine; 1.2 eq [(C$_{18}$H$_{37}$)$_2$MeNH][B(C$_6$F$_5$)$_4$]; 550 eq AlEt$_3$; 100 eq ZnEt$_2$; 40 bar ethene; 60° C.; 5 L autoclave.
Average selectivity for run 36.7 (92.2), 54.6(99.5), 8.5, 0.1, 0.4 [C$_6$(1-C$_6$), C$_8$(1-C$_8$), C$_{10-14}$, C$_{15+}$, PE].

TABLE 24

Effect of dioxygen upon continuous operation tetramerisation catalysis with the triethylaluminium-tetrakis(perfluorophenyl)borate catalyst - addition of dioxygen entrained in the ethylene feed stream.

| Time {min} | $O_2$ in ethene {ppm} | Reactor liquid volume {mL} | Productivity {g/gCr} | Activity {g/gCr/h} | (mol $O_2$) (mol Cr)$^{-1}$ ($10^6$ Prod)$^{-1}$ |
|---|---|---|---|---|---|
| 200 | 1.7 | 2500 | 2,368,636 | 2,704,687 | 2.0 |
| 220 | 1.8 | 2500 | 2,428,026 | 2,556,854 | 2.2 |
| 240 | 1.8 | 2500 | 2,745,351 | 3,157,172 | 2.1 |
| 262 | 1.5 | 2500 | 2,730,681 | 3,198,678 | 1.6 |
| 282 | 1.5 | 2500 | 2,586,430 | 2,877,341 | 1.4 |
| 312 | 1.4 | 2500 | 2,233,770 | 2,415,589 | 2.7 |
| 332 | 1.2 | 2500 | 2,588,063 | 2,854,511 | 1.5 |
| 352 | 1.2 | 2500 | 2,931,108 | 3,510,456 | 1.5 |
| 372 | 1.2 | 2500 | 3,239,306 | 3,818,563 | 1.1 |
| 392 | 3.0 | 2500 | 3,091,901 | 3,633,077 | 3.7 |
| 412 | 2.0 | 2500 | 3,206,644 | 3,642,642 | 2.0 |
| 432 | 2.0 | 2500 | 3,457,282 | 4,630,576 | 2.1 |
| 452 | 2.0 | 2500 | 3,719,936 | 4,838,405 | 2.0 |
| 472 | 2.0 | 2500 | 3,145,765 | 4,064,471 | 1.5 |
| 493 | 1.8 | 2500 | 2,588,205 | 2,633,098 | 1.6 |
| 514 | 0.6 | 2000 | 2,224,056 | 2,485,276 | 1.3 |
| 534 | 1.2 | 2000 | 2,536,063 | 3,412,940 | 1.3 |
| 554 | 2.0 | 2500 | 2,851,486 | 3,879,566 | 2.2 |
| 574 | 1.9 | 2500 | 2,968,161 | 3,754,885 | 2.5 |
| 594 | 6.0 | 2500 | 2,791,318 | 2,983,932 | 4.2 |
| 614 | 3.0 | 2500 | 2,728,533 | 2,955,097 | 3.1 |
| 634 | 2.6 | 2500 | 2,687,278 | 2,795,513 | 2.8 |
| 654 | 2.2 | 2500 | 2,747,933 | 2,870,255 | 1.8 |
| 674 | 3.8 | 2500 | 2,745,584 | 2,863,730 | 4.0 |
| 694 | 1.7 | 2500 | 2,737,827 | 2,772,143 | 1.8 |
| 714 | 1.7 | 2500 | 2,764,090 | 2,804,898 | 1.4 |
| 734 | 2.0 | 2500 | 2,490,317 | 2,575,955 | 1.6 |
| 754 | 1.9 | 2500 | 2,368,290 | 2,289,916 | 1.7 |
| 774 | 2.2 | 2500 | 2,290,701 | 2,350,779 | 2.3 |
| 794 | 2.0 | 2500 | 2,417,300 | 2,261,335 | 1.9 |
| 814 | 2.4 | 2500 | 2,099,956 | 2,123,170 | 2.0 |
| 834 | 2.0 | 2500 | 1,837,569 | 1,559,839 | 1.4 |
| 854 | 1.0 | 2500 | 1,867,086 | 1,737,926 | 1.3 |
| 874 | 1.9 | 2500 | 2,327,848 | 2,392,484 | 2.3 |
| 894 | 6.7 | 2500 | 2,638,587 | 2,827,190 | 5.4 |
| 914 | 2.0 | 2500 | 2,642,322 | 2,651,771 | 1.8 |
| 934 | 2.0 | 2700 | 2,576,187 | 2,496,024 | 1.8 |
| 954 | 2.9 | 2700 | 3,058,963 | 3,211,151 | 3.0 |
| 974 | 1.5 | 2500 | 3,133,638 | 3,445,174 | 1.2 |
| 994 | 5.4 | 2500 | 3,005,245 | 3,122,839 | 4.0 |
| 1015 | 1.4 | 2500 | 2,386,276 | 2,347,547 | 1.4 |
| 1034 | 2.0 | 2500 | 2,358,234 | 2,368,615 | 2.0 |
| 1054 | 1.1 | 2500 | 2,352,966 | 2,301,266 | 1.1 |

TABLE 24-continued

Effect of dioxygen upon continuous operation tetramerisation catalysis with the triethylaluminium-tetrakis(perfluorophenyl)borate catalyst - addition of dioxygen entrained in the ethylene feed stream.

| Time {min} | O$_2$ in ethene {ppm} | Reactor liquid volume {mL} | Productivity {g/gCr} | Activity {g/gCr/h} | (mol O$_2$) (mol Cr)$^{-1}$ (10$^6$ Prod)$^{-1}$ |
|---|---|---|---|---|---|
| 1074 | 1.9 | 2500 | 2,504,281 | 2,465,752 | 2.0 |
| Average | 2.2 | — | 2,663,618 | 2,923,707 | 2.1 |

General conditions: Cr(2-EH)$_3$; 1.2 eq bis(diphenylphosphanyl)(1,2-dimethylheptyl)amine; 1.2 eq [(C$_{18}$H$_{37}$)$_2$MeNH][B(C$_6$F$_5$)$_4$]; 550 eq AlEt$_3$; 100 eq ZnEt$_2$; 40 bar ethene; 60° C.; 5 L autoclave.
Average selectivity for run 38.1 (92.3), 53.3(99.5), 8.4, 0.2, 0.4 [C$_6$(1-C$_6$), C$_8$(1-C$_8$), C$_{10-14}$, C$_{15+}$, PE].

TABLE 25

Effect of dioxygen upon continuous operation tetramerisation catalysis with the methylaluminoxane catalyst - addition of dioxygen entrained in the ethylene feed stream.

| Run Time {h} | (mol O$_2$) (mol Cr)$^{-1}$ (10$^6$ Prod)$^{-1}$ | Productivity {g/gCr} | Activity {g/gCr/h} |
|---|---|---|---|
| 1.3-18.4 | 0.0 | 5,101,672 | 3,774,525 |
| 18.5-23.8 | 0.2 | 5,498,835 | 4,147,642 |
| 26.5-30.9 | 0.3 | 5,691,047 | 4,420,607 |
| 31.3-75.5 | 1.5 | 6,794,525 | 5,702,874 |

General conditions: Cr(acac)$_3$; 1.2 eq bis(diphenylphosphanyl)(1,2-dimethylpropyl)amine; 1900 eq modified methylaluminoxane-20; 46 bar ethene; 0.1 bar H$_2$; 60° C.; 300 L vessel.
Average selectivity for run 22(85), 67(>99), 10, 0.3, 1-2 [C$_6$(1-C$_6$), C$_8$(1-C$_8$), C$_{10-14}$, C$_{15+}$, PE].

TABLE 26

Effect of dioxygen upon continuous operation tetramerisation catalysis with the methylaluminoxane catalyst - addition of dioxygen entrained in the ethylene feed stream.

| Run Time {h} | (mol O$_2$) (mol Cr)$^{-1}$ (10$^6$ Prod)$^{-1}$ | Productivity {g/gCr} | Activity {g/gCr/h} |
|---|---|---|---|
| 2.2-4.4 | 0.0 | 4,398,990 | 3,296,760 |
| 4.5-10.5 | 1.0 | 6,129,356 | 4,729,578 |
| 10.6-19.3 | 2.6 | 5,753,821 | 4,317,000 |
| 19.4-24.5 | 4.2 | 5,999,691 | 4,589,848 |

General conditions: Cr(acac)$_3$; 1.2 eq bis(diphenylphosphanyl)(1,2-dimethylpropyl)amine; 1900 eq modified methylaluminoxane-20; 46 bar ethene; 0.1 bar H$_2$; 60° C.; 300 L vessel.
Average selectivity for run 22(85), 67(>99), 10, 0.3, 1-2 [C$_6$(1-C$_6$), C$_8$(1-C$_8$), C$_{10-14}$, C$_{15+}$, PE].

TABLE 27

Effect of dioxygen upon continuous operation tetramerisation catalysis with the methylaluminoxane catalyst - addition of dioxygen entrained in the ethylene feed stream.

| Run Time {h} | (mol O$_2$) (mol Cr)$^{-1}$ (10$^6$ Prod)$^{-1}$ | Productivity {g/gCr} | Activity {g/gCr/h} |
|---|---|---|---|
| 15.1-18.0 | 0.2 | 4,117,820 | 3,983,355 |
| 18.1-26.0 | 0.3 | 4,495,245 | 4,000,889 |
| 26.1-30.1 | 0.3 | 5,132,919 | 4,563,666 |
| 30.2-33.1 | 0.2 | 4,732,509 | 4,174,120 |
| 33.2-37.3 | 0.3 | 5,167,232 | 4,013,074 |
| 37.4-42.1 | 0.1 | 4,499,150 | 3,289,674 |
| 42.2-44.6 | 0.0 | 4,003,389 | 2,791,357 |
| 44.7-52.4 | 0.3 | 4,481,699 | 3,251,211 |
| 52.5-71.9 | 0.5 | 4,196,374 | 2,967,574 |

General conditions: Cr(acac)$_3$; 1.2 eq bis(diphenylphosphanyl)(1,2-dimethylpropyl)amine; 1900 eq modified methylaluminoxane-20; 46 bar ethene; 0.1 bar H$_2$; 60° C.; 300 L vessel.
Average selectivity for run 22(85), 67(>99), 10, 0.3, 1-2 [C$_6$(1-C$_6$), C$_8$(1-C$_8$), C$_{10-14}$, C$_{15+}$, PE].

The invention claimed is:

1. A process for producing an oligomeric product by oligomerisation of at least one olefinic compound, the process including:
    a) providing an activated oligomerisation catalyst by combining, in any order,
        i) a source of chromium;
        ii) a ligating compound of the formula $(R^1)_m X^1(Y)X^2(R^2)_n$ wherein $X^1$ and $X^2$ are independently an atom selected from the group consisting of nitrogen, phosphorus, and oxygen or an oxidised nitrogen or phosphorus atom where the valence of $X^1$ and/or $X^2$ allows for such oxidation;
    Y is a linking group between $X^1$ and $X^2$;
    m and n are independently 0, 1 or a larger integer; and
    $R^1$ and $R^2$ are independently hydrogen, a hydrocarbyl group, an organoheteryl group, a heterohydrocarbyl group, a substituted hydrocarbyl group, or a substituted heterohydrocarbyl group, and $R^1$ being the same or different when m>1, and $R^2$ being the same or different when n>1; and
        iii) a catalyst activator or combination of catalyst activators; and
    b) contacting at least one olefinic compound with the activated oligomerisation catalyst in the presence of a non-metal oxygen containing additive, which non-metal oxygen containing additive is introduced together with the activated catalyst, after introduction of the activated catalyst but prior to introduction of the olefinic compound, together with the olefinic compound, or after the olefinic compound has contacted the activated catalyst, the non-metal oxygen containing additive being present in an amount such that the ratio of the molar amount of the non-metal oxygen containing additive to the molar amount of chromium pr 10$^6$ g/g Cr productivity in the source of chromium is between 0.01 and 400.

2. A process for activating an oligomerisation catalyst for use in the production of an oligomeric product from at least one olefinic compound, the process comprising combining, in any order,
    i) a source of chromium;
    ii) a ligating compound of the formula $(R^1)_m X^1(Y)X^2(R^2)_n$ wherein $X^1$ and $X^2$ are independently an atom selected from the group consisting of nitrogen, phosphorus, and oxygen, or an oxidised nitrogen or phosphorus atom where the valence of $X^1$ and $X^2$ allows for such oxidation;

Y is a linking group between $X^1$ and $X^2$;

m and n are independently 0, 1 or a larger integer; and $R^1$ and $R^2$ are independently hydrogen, a hydrocarbyl group, an organoheteryl group, a heterohydrocarbyl group, a substituted hydrocarbyl, or a substituted heterohydrocarbyl, and $R^1$ being the same or different when m>1, and $R^2$ being the same or different when n>1;

iii) a catalyst activator or combination of catalyst activators;

iv) a non-metal oxygen containing additive, the non-metal oxygen containing additive being present in an amount such that the ratio of the molar amount of the non-metal oxygen containing additive to the molar amount of chromium per $10^6$ g/g Cr productivity in the source of chromium is between 0.01 and 400.

3. The process of claim 1 or claim 2, wherein the non-metal oxygen containing additive is present in an amount such that the ratio of the molar amount of the non-metal oxygen containing additive to the molar amount of chromium per $10^6$ g/g Cr productivity in the source of chromium is between 0.1 and 200.

4. The process of claim 1 or claim 2, wherein the non-metal oxygen containing additive is present in an amount such that the ratio of the molar amount of the non-metal oxygen containing additive to the molar amount of chromium per $10^8$ g/g Cr productivity in the source of chromium is between 0.1 and 100.

5. The process of claim 1 or claim 2, wherein the non-metal oxygen containing additive is present in an amount such that the ratio of the molar amount of the non-metal oxygen containing additive to the molar amount of chromium per $10^6$ g/g Cr productivity in the source of chromium is between 0.1 and 20.

6. The process of claim 1 or claim 2, wherein the non-metal oxygen containing additive is present in an amount such that the ratio of the molar amount of the non-metal oxygen containing additive to the molar amount of chromium per $10^6$ g/g Cr productivity in the source of chromium is between 0.2 and 10.

7. The process of claim 1 or 2, wherein the non-metal oxygen containing additive is selected from the group consisting of dioxygen ($O_2$), ozone ($O_3$), nitrous oxide ($N_2O$), sulphur dioxide ($SO_2$), epoxide, and mixtures thereof.

8. The process of claim 1 or 2, wherein the non-metal containing oxygen containing additive is a gas and selected from the group consisting of dioxygen ($O_2$), ozone ($O_3$), nitrous oxide ($N_2O$), sulphur dioxide ($SO_2$), ethylene oxide, propylene oxide, and mixtures thereof.

9. The process of claim 1 or claim 2, wherein the non-metal oxygen containing additive is dioxygen ($O_2$) or nitrous oxide ($N_2O$) or mixtures thereof.

10. The process of claim 1 or claim 2, wherein the non-metal oxygen containing additive is dioxygen (oxygen).

11. The process of claim 1 or claim 2, wherein the non-metal oxygen containing additive is added together with the olefinic compound when contacting the activated catalyst.

12. The process of claim 1 or claim 2, wherein the non-metal oxygen containing additive is added after the olefinic compound has contacted the activated catalyst.

13. The process of claim 1 or claim 2, wherein the non-metal oxygen containing additive is added to the activated catalyst prior to the olefinic compound contacting the activated catalyst.

14. The process of claim 1 or claim 2, which includes the use of a solvent.

15. The process of claim 1 or claim 2, which includes the use of a zinc compound.

16. The process of claim 1 or claim 2, wherein the oligomerisation catalyst is a trimerisation catalyst, a tetramerisation catalyst, or both.

17. The process of claim 1 or claim 2, wherein $X^1$ and $X^2$ are independently a phosphorus atom or an oxidised phosphorus atom.

18. The process of claim 1 or claim 2, wherein the ligating compound is of the formula

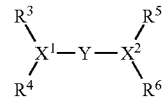

wherein Y is a linking group between $X^1$ and $X^2$, $X^1$ and $X^2$ are independently nitrogen or phosphorus, and $R^3$ to $R^8$ are each independently a hydrocarbyl group, a heterohydrocarbyl group, a substituted hydrocarbyl group or a substituted heterohydrocarbyl group.

19. The process of claim 1 or claim 2, wherein Y is selected from the group consisting of an organic linking group comprising a hydrocarbylene, substituted hydrocarbylene, heterohydrocarbylene or a substituted heterohydrocarbylene; an inorganic linking group comprising either a single- or two-atom linker spacer; and a group comprising methylene; dimethylmethylene; ethylene; ethene-1,2-diyl; propane-1,2-diyl, propane-1,3-diyl; cyclopropane-1,1-diyl; cyclopropane-1,2-diyl; cyclobutane-1,2-diyl, cyclopentane-1,2-diyl, cyclohexane-1,2-diyl, cyclohexane-1,1-diyl; 1,2-phenylene; naphthalene-1,8-diyl; phenanthrene-9,10-diyl, phenanthrene-4,5-diyl, 1,2-catecholate, 1,2-diarylhydrazine-1,2-diyl (—N(Ar)—N(Ar)—) where Ar is an aryl group; 1,2-dialkylhydrazine-1,2-diyl (—N(Alk)-N(Alk)-) where Alk is an alkyl group; —B($R^7$)—, —Si($R^7$)$_2$—, —P($R^7$)— and —N($R^7$)— where $R^7$ is, a hydrocarbyl, substituted hydrocarbyl, heterocarbyl, substituted heterocarbyl or halogen.

20. The process of claim 18, wherein the ligating compound is of the formula

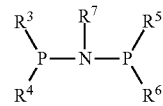

wherein $R^3$ to $R^7$ are each independently a hydrocarbyl group, a heterohydrocarbyl group, a substituted hydrocarbyl group or a substituted heterohydrocarbyl group.

21. The process of claim 20, wherein each of $R^3$ to $R^6$ is an alkyl selected from the group consisting of methyl, ethyl and isopropyl or an aromatic selected from the group consisting of phenyl and substituted phenyl.

22. The process of claim 1 or claim 2, wherein the activator is selected from the group consisting of organoboron compounds, aluminoxanes including modified aluminoxanes, aluminium alkyls, other metal or main group alkyl or aryl compounds, ionizing activators which are neutral or ionic, Lewis acids, reducing acids, oxidising agents and combinations thereof.

23. The process of claim 7, wherein the epoxide is selected from ethylene oxide, propylene oxide, butylene oxide, and the epoxide of any other olefin.

24. The process of claim 7, wherein the peroxide is selected from $H_2O_2$ and organic peroxides ROOH, wherein R is a hydrocarbyl or heterohydrocarbyl.

25. The process of claim 7, wherein the amine oxide is selected from pyridinium N-oxide, TEMPO, and $R_3NO$.

* * * * *

UNITED STATES PATENT AND TRADEMARK OFFICE
CERTIFICATE OF CORRECTION

PATENT NO. : 9,447,202 B2  
APPLICATION NO. : 14/399103  
DATED : September 20, 2016  
INVENTOR(S) : Martin John Hanton et al.

It is certified that error appears in the above-identified patent and that said Letters Patent is hereby corrected as shown below:

In the Claims

Claim 4, Column 37, Line 27, "$10^8$" should read --$10^6$--.

Claim 18, Column 38, Line 21, "$R^8$" should read --$R^6$--.

Signed and Sealed this  
Third Day of January, 2017

Michelle K. Lee  
*Director of the United States Patent and Trademark Office*